(12) United States Patent
Khanna et al.

(10) Patent No.: US 11,478,508 B2
(45) Date of Patent: Oct. 25, 2022

(54) METHODS OF IMMUNOTHERAPY

(71) Applicant: The Council of the Queensland Institute of Medical Research, Herston (AU)

(72) Inventors: Rajiv Khanna, Herston (AU); Corey Smith, Ashgrove (AU)

(73) Assignee: The Council of the Queensland Institute of Medical Research, Herston (AU)

( * ) Notice: Subject to any disclaimer, the term of this patent is extended or adjusted under 35 U.S.C. 154(b) by 761 days.

(21) Appl. No.: 16/303,693

(22) PCT Filed: May 25, 2017

(86) PCT No.: PCT/IB2017/000705
§ 371 (c)(1),
(2) Date: Nov. 21, 2018

(87) PCT Pub. No.: WO2017/203356
PCT Pub. Date: Nov. 30, 2017

(65) Prior Publication Data
US 2021/0228628 A1    Jul. 29, 2021

Related U.S. Application Data

(60) Provisional application No. 62/487,814, filed on Apr. 20, 2017, provisional application No. 62/341,360, filed on May 25, 2016.

(51) Int. Cl.
| | | |
|---|---|---|
| *A61K 38/19* | (2006.01) | |
| *A61K 38/20* | (2006.01) | |
| *A61K 38/21* | (2006.01) | |
| *A61K 35/17* | (2015.01) | |
| *A61P 35/00* | (2006.01) | |
| *A61K 38/17* | (2006.01) | |
| *A61K 38/48* | (2006.01) | |
| *C12N 5/0783* | (2010.01) | |
| *G01N 33/50* | (2006.01) | |

(52) U.S. Cl.
CPC .......... *A61K 35/17* (2013.01); *A61K 38/1709* (2013.01); *A61K 38/191* (2013.01); *A61K 38/2013* (2013.01); *A61K 38/217* (2013.01); *A61K 38/482* (2013.01); *A61P 35/00* (2018.01); *C12N 5/0636* (2013.01); *G01N 33/505* (2013.01); *G01N 33/5023* (2013.01); *G01N 2333/525* (2013.01); *G01N 2333/55* (2013.01); *G01N 2333/57* (2013.01); *G01N 2333/70514* (2013.01); *G01N 2333/70517* (2013.01); *G01N 2333/70596* (2013.01); *G01N 2333/96436* (2013.01)

(58) Field of Classification Search
CPC . A61K 38/191; A61K 38/2013; A61K 38/217
See application file for complete search history.

(56) References Cited

U.S. PATENT DOCUMENTS

| | | |
|---|---|---|
| 10,568,908 B2 | 2/2020 | O'Reilly et al. |
| 2003/0134415 A1 | 7/2003 | Gruenberg |
| 2009/0324630 A1 | 12/2009 | Jensen |
| 2014/0044687 A1 | 2/2014 | Forte et al. |
| 2014/0099341 A1 | 4/2014 | Slanetz |
| 2014/0356398 A1 | 12/2014 | Riddell et al. |
| 2015/0064206 A1 | 3/2015 | Foussat et al. |
| 2018/0125891 A1 | 5/2018 | O'Reilly et al. |
| 2021/0220402 A1 | 7/2021 | Khanna |
| 2021/0228628 A1 | 7/2021 | Khanna et al. |

FOREIGN PATENT DOCUMENTS

| | | |
|---|---|---|
| EA | 005821 B1 | 6/2005 |
| EP | 2367000 A1 | 9/2011 |
| RU | 2558294 C1 | 7/2015 |
| WO | WO-1999/013904 A1 | 3/1999 |
| WO | WO-2004/015070 A2 | 2/2004 |
| WO | WO-2006/124827 A2 | 11/2006 |
| WO | WO2009094273 * | 7/2009 |
| WO | WO-2013/088114 A1 | 6/2013 |
| WO | WO-2014/043708 A1 | 3/2014 |
| WO | WO-2014/203214 A1 | 12/2014 |
| WO | WO-2016/020056 A1 | 2/2016 |
| WO | WO-2016/073550 A1 | 5/2016 |
| WO | WO-2016/191756 A1 | 12/2016 |
| WO | WO-2017/203356 A1 | 11/2017 |
| WO | WO-2017/203368 A1 | 11/2017 |
| WO | WO-2018/136762 A1 | 7/2018 |

OTHER PUBLICATIONS

Lagoo et al. J Immunol 1994; 152:1641-1652.*
Rodriguez et al 2005, Clinical and Diagnostic Laboratory Immunology, vol. 12, No. 4, pp. 502-507.*
Leng et al (2008) Journal of Genrontology: Medical Sciences, vol. 63A, No. 8, pp. 879-884.*
Extended European Search Report for EP Application No. EP 17802272 dated Feb. 17, 2020.
Amir et al., "Allo-HLA reactivity of virus-specific memory T cells is common," Blood, 115(15): 3146-3157 (2010).
Baecher-Allen et al., "Multiple Sclerosis: Mechanisms and Immunotherapy," Neuron, 97(4): 742-768 (2018).
Chuntova et al., "Genetically Engineered T-Cells for Malignant Glioma: Overcoming the Barriers to Effective Immunotherapy," Frontiers in Immunology, 9 (Article 3062): 1-9 (2019).
Extended European Search Report for EP Application No. 17802266.1 dated Jun. 26, 2020.
Extended European Search Report for EP Application No. EP 18741137 dated Jul. 7, 2020.
Oliveria et al., "In Vivo Immunogenic Response to Allogeneic Mesenchymal Stem Cells and the Role of Preactivated Mesenchymal Stem Cells Cotransplanted with Allogeneic Islets," Stem Cells International, 2017 (Article ID 9824698): 12 pages (2017).

(Continued)

*Primary Examiner* — Prema M Mertz
(74) *Attorney, Agent, or Firm* — Foley Hoag LLP; David P. Halstead

(57) ABSTRACT

Provided herein are methods and compositions related to the selection T cells and/or subjects for adoptive immunotherapy based on the expression of one or more biomarkers.

19 Claims, 9 Drawing Sheets

(56) References Cited

OTHER PUBLICATIONS

Pender et al., "Phase 1 Study of the Safety and Efficacy of ATA188, an Off-the-shelf, Allogeneic Epstein-Barr Virus-targeted T-cell Immunotherapy to Treat Progressive Forms of Multiple Sclerosis," European Academyn of Neurology Meeting, Poster Abstract #LB130 (2020).
Pender et al., "Phase 1 study of the safety and efficacy of ATA188, an off-the-shelf, allogeneic Epstein-Barr virus-targeted T-cell immunotherapy to treat progressive forms of multiple sclerosis," European Journal of Neurology, 27(1): 1302-1303 (2020).
Pender et al., "Preliminary Phase 1 Safety of ATA188, a Pre-manufactured, Unrelated Donor (Off-the-Shelf, Allogeneic)Epstein-Barr Virus-targeted T-cell Immunotherapy for Patients With Progressive Forms of Multiple Sclerosis," 5th Congress of the European Academy of Neurology (EAN), Poster Abstract #1303 (2019).
Pender et al., "Preliminary phase 1 safety of ATA188, a pre-manufactured, unrelated donor (offthe-shelf, allogeneic) Epstein-Barr virus (EBV)-targeted T-cell immunotherapy for patients with progressive multiple sclerosis (MS)," European Journal of Neurology, 26(1): 683 (2019).
Pender et al., "Preliminary Safety and Efficacy Of ATA188, a Pre-manufactured, Unrelated Donor (Off-the-shelf, Allogeneic) Epstein-Barr Virus-targeted T-cell Immunotherapy for Patients With Progressive Forms of Multiple Sclerosis," 35th Congress of the European Committee for Treatment and Research in Multiple Sclerosis (ECTRIMS) / 24th Annual Conference of Rehabilitation in MS, Poster Abstract #A-1026-0000-02651 (2019).
Pender et al., "Preliminary safety and efficacy of ATA188, a pre-manufactured, unrelated donor (off-the-shelf, allogeneic) Epstein-Barr virus-targeted T-cell immunotherapy for patients with progressive forms of multiple sclerosis," Multiple Sclerosis Journal, 25(S2): 931 (2019).
Roskrow et al., "Epstein-Barr Virus (EBV)-Specific Cytotoxic T Lymphocytes for the Treatment of Patients With EBV-Positive Relapsed Hodgkin's Disease," Blood, 91(8): 2925-2934 (1998).
Tovey et al., "Immunogenicity and other problems associated with the use of biopharmaceuticals," Therapeutic Advances in Drug Safety, 2(3): 113-128 (2011).
Voge et al., "Monoclonal Antibodies in Multiple Sclerosis: Present and Future," Biomedicines, 7(1): 1-13 (2019).
Bitsch et al., "Differentiation of multiple sclerosis subtypes: implications for treatment," CNS Drugs, 16(6):405-418 (2002).
Bratke et al., "Differential expression of human granzymes A, B, and K in natural killer cells and during CD8+ T cell differentiation in peripheral blood," Eur J Immunol, 35:2608-2616 (2005).
Draborg et al., "Epstein-Barr virus in systemic autoimmune diseases," Clin Dev Immunol, Article ID:535738 (2013).
Harari et al., "Distinct profiles of cytotoxic granules in memory CD8 T cells correlate with function, differentiation stage, and antigen exposure," J Virol, 83(7):2862-2871 (2009).
Holmes-Liew et al., "Adoptive T-cell immunotherapy for ganciclovir-resistant CMV disease after lung transplantation," Clin Transl Immunology, 4(3): e35 (2015).
International Search Report and Written Opinion for International Application No. PCT/IB2017/000705 dated Sep. 29, 2017.
International Search Report and Written Opinion for International Application No. PCT/US2018/014458 dated May 4, 2018.
International Search Report for International Application No. PCT/IB2007/000805 dated Nov. 7, 2017.
Jaquiéry et al., "Intrathecal immune responses to EBV in early MS," Eur J Immunol, 40(3):878-887 (2010).
Jilek et al., "HLA-B7-restricted EBV-specific CD8+ T cells are dysregulated in multiple sclerosis," J Immunol, 188(9):4671-4680 (2012).
Leen et al., "Adoptive immunotherapy for herpesviruses. In: Human Herpesviruses: Biology, Therapy, and Immunoprophylaxis," Cambridge University Press (2007).
Legroux et al., "Multiple sclerosis and T lymphocytes: an entangled story," J Neuroimmune Pharmacol, 10(4):528-546 (2015).
Lelic et al., "The polyfunctionality of human memory CD8+ T cells elicited by acute and chronic virus infections is not influenced by age," PLoS Pathog, 8(12):e1003076 (2012).
O'Reilly et al., "Virus-specific T-cell banks for 'off the shelf' adoptive therapy of refractory infections," Bone Marrow Transpl, 51 (9): 1163-1172 (2016).
Pender et al., "Epstein-Barr virus and multiple sclerosis: potential opportunities for immunotherapy," Clin Transl Immunology, 3(10):e27 (2014).
Pender et al., "Epstein-Barr virus-specific adoptive immunotherapy for progressive multiple sclerosis," Mult Scler, 20(11):1541-1544 (2014).
Pender et al., "Epstein-Barr virus-specific adoptive immunotherapy: a new horizon for multiple sclerosis treatment?," Immunotherapy, 6(6):659-661 (2014).
Smith et al., "Adoptive cellular immunotherapy for virus-associated cancers: a new paradigm in personalized medicine," Immunol Cell Biol, 95:364-371 (2017).
Smith et al., "Effective treatment of metastatic forms of Epstein-Barr virus-associated nasopharyngeal carcinoma with a novel adenovirus-based adoptive immunotherapy," Cancer Res, 72(5):1116-1125 (2012).
Smith et al., "Ex vivo expansion of human T cells for adoptive immunotherapy using the novel Xeno-free CTS Immune Cell Serum Replacement," Clin Transl Immunology, 4(1): e31 (2015).
Smith et al., "Pre-emptive and therapeutic adoptive immunotherapy for nasopharyngeal carcinoma: Phenotype and effector function of T cells impact on clinical response," Oncoimmunology, 6(2):Article e1273311, (2017).
Vanhoutte et al., "Cytolytic mechanisms and T-cell receptor Vβ usage by ex vivo generated Epstein-Barr virus-specific cytotoxic T lymphocytes," Immunology, 127:577-586 (2009).
Dinesh et al., "CD8+ Tregs in Lupus, Autoimmunity, and Beyond," Autoimmun Rev. 9(8): 560-568 (21 pages)(2010).
International Preliminary Report on Patentability for International Application No. PCT/US2018/014458 dated Jul. 23, 2019.
Moosmann et al., "Abstract," Blood, 115(14):2960-2970 (2010).
Supplementary European Search Report for EP application No. EP 17802266 dated Dec. 18, 2019.
Angelini et al., "Increased CD8+ T Cell Response to Epstein-Barr Virus Lytic Antigens in the Active Phase of Multiple Sclerosis," PLOS Pathogens, 9(4): e1003220 pp. 1-16 (2013).
Faustman., "EBV infection and anti-CD3 treatment for Type 1 diabetes: bad cop, good cop?," Expert Review of Clinical Immunology, 9(2): 95-97 (2013).
Friese et al., "Autoreactive CD8+ cells in multiple sclerosis: a new target for therapy?," Brain, 128: 1747-1763 (2005).
Haque et al., "Allogeneic cytotoxic T-cell therapy for EBV-positive posttransplantation lymphoproliferative disease: results of a phase 2 multicenter clinical trial," Blood, 110(4): 1123-1131 (2007).
U.S. Department of Health and Human Services., "Progress in Autoimmune Diseases Research," National Institutes of Health The Autoimmune Diseases Coordinating Committee: 146 pages (2005).

\* cited by examiner

A

B

C

A

B

A

B

METHODS OF IMMUNOTHERAPY

RELATED APPLICATIONS

This application is a § 371 national-stage application based on PCT/IB2017/00705 filed May 25, 2017 which claims the benefit of priority to U.S. Provisional Patent Application Ser. No. 62/341,360, filed May 25, 2016, and U.S. Provisional Patent Application Ser. No. 62/487,814, filed Apr. 20, 2017, each of which is hereby incorporated by reference in its entirety.

BACKGROUND

Adoptive immunotherapy involves implanting or infusing disease-specific T cells, such as cytotoxic T cells (CTLs), into individuals with the aim of recognizing, targeting, and destroying disease-associated cells. Adoptive immunotherapy has become a promising route for the treatment of many diseases and disorders, including cancer, infectious diseases and autoimmune diseases. However, the efficiency of adoptive immunotherapy can vary from cell sample to cell sample, thus creating a need for methods of predicting the likely therapeutic efficacy of an immunotherapeutic sample.

SUMMARY

In certain aspects, provided herein are methods related to selecting samples comprising T cells (e.g., CD4 T cells or CD8 T cells, such as CTLs) for use in adoptive immunotherapy and/or for inclusion into a cell bank based on the expression of CD107a, interferon gamma (IFNg), interleukin 2 (IL-2) tumor necrosis factor (TNF), granzyme B (GzmB), granzyme K (GzmK) and/or perforin (Prf) by the total lymphocytes. T cells, CD8 T cells and/or CD4 T cells in the samples. In some embodiments, the samples are selected based on the expression of CD8, CD4, PD-1, TIM-3, LAG-3 and/or CTLA-4 by the total lymphocytes, T cells, CD8 T cells and/or CD4 cells in the samples. In some embodiments, the samples are selected based on the expression of antigen-specific T cell receptors (TCR) by the total lymphocytes, T cells, CD8 T cells and/or CD4 T cells in the samples. In some embodiments, the samples are selected if the expression of CD107a, interferon gamma IFNg, IL-2, TNF, GzmB, GzmK, Prf, CD8, CD4, PD-1, TIM-3, LAG-3, CTLA-4 and/or antigen-specific TCR is above a threshold level provided herein. In some embodiments, the samples are selected if the expression of IFNg, IL-2, TNF and CD-107a is above a threshold level provided herein. In some embodiments, the samples are not selected if the expression of CD107a, interferon gamma (IFNg), interleukin 2 (IL-2), tumor necrosis factor (TNF), granzyme B (GzmB), granzyme K (GzmK), perforin (Prf), CD8, CD4, PD-1, TIM-3, LAG-3, CTLA-4 and/or antigen-specific TCR is below a threshold level provided herein. In some embodiments, the samples are not selected if the expression of IFNg, IL-2, TNF and CD-107a is below a threshold level provided herein. In certain aspects, provided herein are methods of treating a subject in need thereof (e.g., a subject with cancer, a viral infection and/or an autoimmune disease) by administering to the subject a sample comprising T cells (e.g., CD4 T cells or CD8 T cells, such as CTLs) selected according to a method described herein. In certain embodiments, provided herein is a method of generating a cell bank of samples comprising T cells (e.g., CD4 T cells or CD8 T cells, such as CTLs) for adoptive immunotherapy, the method comprising adding one or more samples selected according to a method provided herein to a cell bank. In some aspects, provided herein is a cell bank generated according to a method described herein.

In certain aspects, provided herein are methods related to selecting samples comprising T cells (e.g., CD8 and/or CD4 T cells) for use in adoptive immunotherapy and/or for inclusion into a cell bank based on the expression of IFNg, IL-2, TNF, GzmB, GzmK, Prf, CD8, CD4, PD-1, TIM-3, CTLA-4 and/or antigen-specific TCR by the total lymphocytes, T cells, CD8 T cells and/or CD4 T cells in the samples. In some embodiments, the samples are selected if the expression of IFNg, IL-2, TNF, GzmB, GzmK, Prf, CD8, CD4, PD-1, TIM-3, LAG-3, CTLA-4 and/or antigen-specific TCR is above a threshold level provided herein. In some embodiments, the samples are selected if the expression of IFNg, IL-2, TNF and CD-107a is above a threshold level provided herein. In some embodiments, the samples are not selected if the expression of IFNg, IL-2, TNF, GzmB, GzmK, Prf, CD8, CD4, PD-1, TIM-3, LAG-3, CTLA-4 and/or antigen-specific TCR is below a threshold level provided herein. In some embodiments, the samples are not selected if the expression of IFNg, IL-2, TNF and CD-107a is below a threshold level provided herein. In certain aspects, provided herein are methods of treating a subject in need thereof (e.g., a subject with cancer, a viral infection and/or an autoimmune disease) by administering to the subject a sample comprising T cells (e.g., CD8 and/or CD4 T cells) selected according to a method described herein. In certain embodiments, provided herein is a method of generating a cell bank of samples comprising T cells (e.g., CD8 and/or CD4 T cells) for adoptive immunotherapy, the method comprising adding one or more samples selected according to a method provided herein to a cell bank. In some aspects, provided herein is a cell bank generated according to a method described herein.

In some aspects, provided herein are methods of selecting a sample comprising T cells (e.g., CD8 and/or CD4 T cells) for ex vivo expansion (e.g., a large scale expansion for inclusion in a cell bank or for adoptive transfer) based on the expression of IFNg, IL-2, TNF, GzmB, GzmK, Prf, CD8, CD4, PD-1, TIM-3, LAG-3, CTLA-4 and/or antigen-specific TCR by a portion of the total lymphocytes, T cells, CD8 T cells and/or CD4 T cells in the sample. For example, in some embodiments the samples are selected by first performing a small scale expansion and/or inducing proliferation in T cells from a portion of the sample, measuring the expression of one or more of IFNg, IL-2, TNF, GzmB, GzmK, Prf, CD8, CD4, PD-1, TIM-3, LAG-3, CTLA-4 and/or antigen-specific TCR by the portion of the total lymphocytes, T cells, CD8 T cells and/or CD4 T cells. In some embodiments, the samples are selected if the expression of IFNg, IL-2, TNF, GzmB, GzmK, Prf, CD8, CD4, PD-1, TIM-3, LAG-3, CTLA-4 and/or antigen-specific TCR is above a threshold level provided herein. In some embodiments, the samples are selected if the expression of IFNg, IL-2, TNF and CD-107a is above a threshold level provided herein. In some embodiments, the samples are not selected if the expression of IFNg, IL-2, TNF, GzmB, GzmK, Prf, CD8, CD4, PD-1, TIM-3, LAG-3, CTLA-4 and/or antigen-specific TCR is below a threshold level provided herein. In some embodiments, the samples are not selected if the expression of IFNg. IL-2. TNF and CD-107a is below a threshold level provided herein.

In some aspects, provided herein are methods of selecting a subject for autologous adoptive T cell immunotherapy (e.g., using CD8 or CD4 T cells) and/or as a T cell donor based on the expression of IFNg, IL-2, TNF, GzmB, GzmK, Prf, CD8, CD4, PD-1, TIM-3, LAG-3, CTLA-4 and/or antigen-specific TCR by the total lymphocytes, T cells, CD8 T cells and/or CD4 T cells in a sample obtained from the subject. For example, in some embodiments the subject is selected by first performing an expansion and/or inducing proliferation in T cells (e.g., CD8 and/or CD4 T cells) in a sample obtained from the subject, and measuring the expression of one or more of IFNg, IL-2, TNF, GzmB, GzmK, Prf, CD8, CD4, PD-1, TIM-3, LAG-3, CTLA-4 and/or antigen-specific TCR by the total lymphocytes, T cells, CD8 T cells and/or CD4 T cells. In some embodiments, the subject is selected if the expression of IFNg, IL-2, TNF, GzmB, GzmK, Prf, CD8, CD4, PD-1, TIM-3, LAG-3, CTLA-4 and/or antigen-specific TCR is above a threshold level provided herein. In some embodiments, the subjects are selected if the expression of IFNg, IL-2, TNF and CD-107a is above a threshold level provided herein. In some embodiments, the subject is not selected if the expression of IFNg, IL-2, TNF, GzmB, GzmK, Prf, CD8, CD4, PD-1, TIM-3, LAG-3, CTLA-4 and/or antigen-specific TCR is below a threshold level provided herein. In some embodiments, the subjects are not selected if the expression of IFNg, IL-2, TNF and CD-107a is below a threshold level provided herein.

In some embodiments, the threshold level is met if at least about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20%, 21%, 22%, 23%, 24% or 25% of the total lymphocytes, T cells, CD8 T cells and/or CD4 T cells express CD107a.

In some embodiments, the threshold level is met if at least about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20%, 21%, 22%, 23%, 24% or 25% of the total lymphocytes, T cells, CD8 T cells and/or CD4 T cells express IFNg.

In some embodiments, the threshold level is met if at least about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20%, 21% 22%, 23%, 24% or 25% of the total lymphocytes, T cells, CD8 T cells and/or CD4 T cells express IL-2.

In some embodiments, the threshold level is met if at least about 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20%, 21%, 22%, 23%, 24% or 25% of the total lymphocytes, T cells. CD8 T cells and/or CD4 T cells express TNF.

In some embodiments, the threshold level is met if at least about 5%, 6%, 7%, 8%, 9%, 10%, 11%, 12%, 13%, 14%, 15%, 16%, 17%, 18%, 19%, 20%, 21%, 22%, 23%, 24% or 25% of the total lymphocytes, T cells, CD8 T cells and/or CD4 T cells express granzyme B.

In some embodiments, the threshold level is met if at least about 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells express granzyme K.

In some embodiments, the threshold level is met if at least about 2%, 3%, 4%, 5%, 6%, 7%, 8%, 9%, 10%, 11%, 12%, 13%, 14% or 15% of the total lymphocytes, T cells, CD8 T cells and/or CD4 T cells express perforin.

In some embodiments, the threshold level is met if at least about 15%, 16%, 17%, 18%, 19%, 20%, 21%, 22%, 23%, 24%, 25%, 26%, 27%, 28%, 29%, 30%, 40%, 50%, 60%, 70% or 80% of the total lymphocytes in the sample express CD8.

In some embodiments, the threshold level is met if at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% of the total lymphocytes in the sample express CD4.

In some embodiments, the threshold level is met if at least about 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells express PD-1.

In some embodiments, the threshold level is met if at least about 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells express TIM-3.

In some embodiments, the threshold level is met if at least about 3%, 4%, 5%, 6%, 7%, 8%, 9%, 10%, 11%, 12%, 13%, 14%, 15%, 16%, 17%, 18%, 19% or 20% of t the total lymphocytes, T cells, CD8 T cells and/or CD4 T cells express LAG-3.

In some embodiments, the threshold level is met if at least about 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells express CTLA-4.

In some embodiments, the threshold level is met if at least about 3%, 40, 5%, 6%, 7%, 8%, 9%, 10%, 11%, 12%, 13%, 14%, 15%, 16%, 17%, 18%, 19% or 20% of the total lymphocytes. T cells, CD8 T cells and/or CD4 T cells express CTLA-4.

In some embodiments, the threshold level is met if at least about 15%, 16%, 17%, 180, 19%, 20%, 21%, 22%, 23%, 24%, 25%, 26%, 27%, 28%, 29%, 30%, 40%, 50%, 60%, 70% or 80% of the total lymphocytes, T cells, CD8 T cells and/or CD4 T cells in the sample express an antigen-specific TCR.

In certain aspects, provided herein is a method of treating a disease or disorder in a subject in need thereof comprising administering to the subject in need thereof a sample obtained from a cell bank provided herein and/or the T cells (e.g., CD4 T cells or CD8 T cells, such as CTLs) from a cell bank provided herein. In some embodiments, the disease or disorder is cancer (e.g., EBV-associated cancer, such as nasopharyngeal carcinoma, NK/T cell lymphoma, EBV-associated gastric carcinoma, or EBV-associated leiomyosarcoma). In some embodiments, the subject has post-transplant lymphoproliferative disorder (PTLD). In some embodiments, the subject has post-transplant lymphoproliferative disorder (PTLD) and an immunodeficiency disorder (e.g., HIV/AIDS or X-linked inhibitor Apoptosis (XIAP)). In some embodiments, the subject has an autoimmune disorder, such as multiple sclerosis, rheumatoid arthritis, systemic lupus erythematosus, celiac disease, other systemic autoimmune diseases (SAD), or inflammatory bowel disease (IBD). In some embodiments, the T cells (e.g., CD4 T cells or CD8 T cells, such as CTLs) are allogeneic to the subject.

In some embodiments, the expression of IFNg, IL-2, TNF, GzmB, GzmK, Prf, CD8, CD4, PD-1, TIM-3, LAG-3, CTLA-4 and/or antigen-specific TCR is determined by Fluorescence Activated Cell Sorting (FACS). In some embodiments, the expression of IFNg, IL-2, TNF, GzmB, GzmK, Prf, CD8, CD4, PD-1, TIM-3, LAG-3, CTLA-4 and/or antigen-specific TCR is determined by ELISpot. In some embodiments, the T cells (e.g., CD8 and/or CD4 T cells) in the sample express a TCR specific for an Epstein-Barr virus (EBV) peptide (e.g., a LMP1 peptide, a LMP2A peptide or an EBNA1 peptide) presented on a MHC (e.g., a class I or a class II MHC).

In some embodiments, the selected sample is administered to a subject in need thereof. In some embodiments, the T cells (e.g., CD8 and/or CD4 T cells) are allogeneic to the subject (e.g., the sample comprising the T cells is obtained from a cell bank). In some embodiments, the T cells (e.g., CD8 and/or CD4 T cells) are autologous to the subject.

In certain aspects, provided herein is a method of generating a sample comprising T cells (e.g., CD8 and/or CD4 T cells) for adoptive immunotherapy, the method comprising incubating a sample comprising T cells (e.g., CD8 and/or CD4 T cells) with antigen-presenting cells (APCs) presenting a peptide antigen on a MHC (e.g., class I and/or class II MHC) such that T cells expressing a TCR specific for the peptide antigen presented on the MHC proliferate and then determining the expression of IFNg, IL-2, TNF, GzmB, GzmK, Prf, CD8, CD4, PD-1, TIM-3, LAG-3, CTLA-4 and/or antigen-specific TCR by T cells in the sample. In some embodiments, the peptide is an EBV peptide (e.g., a LMP1 peptide, a LMP2A peptide or an EBNA1 peptide).

In certain aspects, provided herein is a method of treating a disease or disorder in a subject in need thereof comprising administering to the subject in need thereof T cells from a sample selected according to a method provided herein and/or obtained from a cell bank provided herein. In some embodiments, the disease or disorder is cancer (e.g., EBV-associated cancer, such as nasopharyngeal carcinoma, NK/T cell lymphoma. EBV-associated gastric carcinoma, or EBV-associated leiomyosarcoma). In some embodiments, the subject has post-transplant lymphoproliferative disorder (PTLD). In some embodiments, the subject has post-transplant lymphoproliferative disorder (PTLD) and an immunodeficiency disorder (e.g., HIV/AIDS or X-linked inhibitor Apoptosis (XIAP)). In some embodiments, the subject has an autoimmune disorder, such as multiple sclerosis, rheumatoid arthritis, systemic lupus erythematosus, celiac disease, other systemic autoimmune diseases (SAD), or inflammatory bowel disease (IBD). In some embodiments, the T cells are allogeneic to the subject.

In certain aspects, provided herein is a cell bank of samples comprising T cells (e.g., CD8 and/or CD4 T cells) that is enriched for samples in which at least a threshold level of lymphocytes in the sample express IFNg, IL-2, TNF, GzmB, GzmK, Prf, CD8, CD4, PD-1, TIM-3, LAG-3, CTLA-4 and/or antigen-specific TCR. In certain embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80% 81%, 82%, 83%, 84%, 85%, 86%, 87%, 88%, 89%, 90%, 91%, 92%, 93%, 94%, 95%, 96%, 97%, 98%, 99% or 100% of the samples in the cell bank are samples comprising T cells (e.g., CD8 and/or CD4 T cells) in which at least a threshold level of lymphocytes in the sample express IFNg, IL-2, TNF, GzmB, GzmK, Prf, CD8, CD4, PD-1, TIM-3, LAG-3, CTLA-4 and/or antigen-specific TCR.

Provided herein are methods of selecting subject for adoptive immunotherapy by performing an expansion and/or inducing proliferation in T cells (e.g., CD8 and/or CD4 T cells) in a sample obtained from the subject, and measuring the expression of one or more of IFNg, IL-2, TNF, GzmB, GzmK, Prf, CD8, CD4, PD-1, TIM-3, LAG-3, CTLA-4 and/or antigen-specific TCR by the T cells. In some embodiments, the subject is selected if the expression of IFNg, IL-2, TNF, GzmB, GzmK, Prf, CD8, CD4, PD-1, TIM-3, LAG-3, CTLA-4 and/or antigen-specific TCR is above a threshold level provided herein. In some embodiments, the subject is not selected if the expression of IFNg, IL-2, TNF, GzmB, GzmK, Prf, CD8, CD4, PD-1, TIM-3, LAG-3, CTLA-4 and/or antigen-specific TCR is below a threshold level provided herein. In some embodiments, the subject has a disease or disorder. In some embodiments, the disease or disorder is cancer (e.g., EBV-associated cancer, such as nasopharyngeal carcinoma, NK/T cell lymphoma, EBV-associated gastric carcinoma, or EBV-associated leiomyosarcoma). In some embodiments, the subject has post-transplant lymphoproliferative disorder (PTLD). In some embodiments, the subject has post-transplant lymphoproliferative disorder (PTLD) and an immunodeficiency disorder (e.g., HIV/AIDS or X-linked inhibitor Apoptosis (XIAP)). In some embodiments, the subject has an autoimmune disorder, such as multiple sclerosis, rheumatoid arthritis, systemic lupus erythematosus, celiac disease, other systemic autoimmune diseases (SAD), or inflammatory bowel disease (IBD).

DETAILED DESCRIPTION

Definitions

Figure 1:
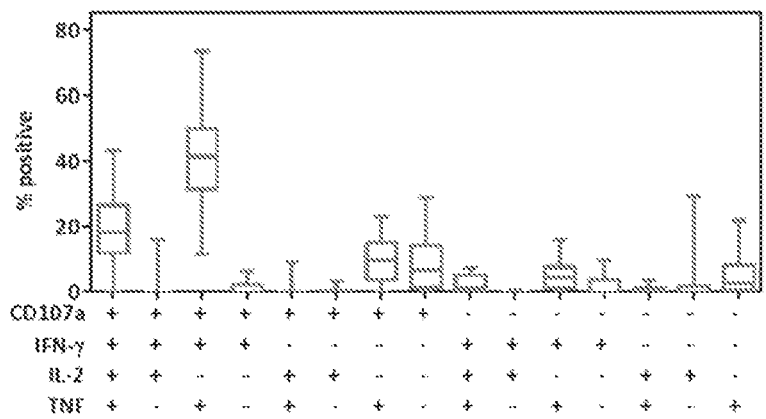
FIG. 1 has three panels showing that E1-LMPpoly expanded T cells are functionally competent and express immune checkpoint molecules. Panel A depicts percentage of HLA-multimer positive CD8-positive lymphocytes that have express CD107a, IFN-γ, IL-2 and/or TNF. Panel B depicts percentage of HLA-multimer positive CD8-positive lymphocytes that express granzyme B (GzmB), granzyme K (GzmK) and/or perforin (Prf). Panel C depicts percentage of HLA-multimer positive CD8-positive lymphocytes that express PD-1, TIM-3, LAG-3 and CTLA-4.
Figure 1:
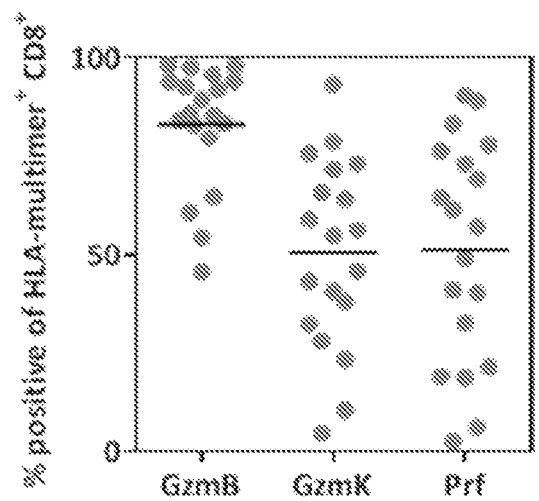
Figure 1:
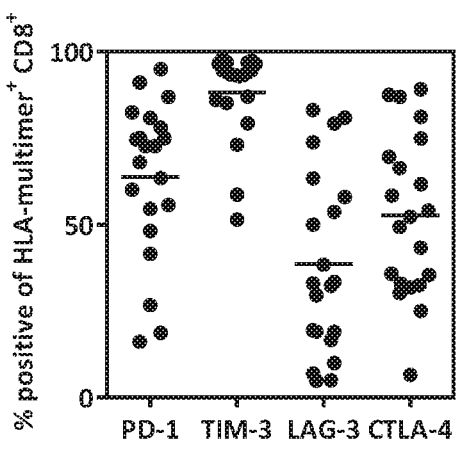

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

In some embodiments, the CTL composition further comprises an adjuvant. As used herein, the term "adjuvant" broadly refers to an agent that affects an immunological or physiological response in a patient or subject. For example, an adjuvant might increase the presence of an antigen over time or to an area of interest like a tumor, help absorb an antigen-presenting cell antigen, activate macrophages and lymphocytes and support the production of cytokines. By changing an immune response, an adjuvant might permit a smaller dose of an immune interacting agent to increase the effectiveness or safety of a particular dose of the immune interacting agent. For example, an adjuvant might prevent T cell exhaustion and thus increase the effectiveness or safety of a particular immune interacting agent. Examples of adjuvants include, but are not limited to, an immune modulatory protein, Adjuvant 65, α-GalCer, aluminum phosphate, aluminum hydroxide, calcium phosphate, β-Glucan Peptide, CpG DNA, GPI-0100, lipid A, lipopolysaccharide, Lipovant, Montanide, N-acetyl-muramyl-L-alanyl-D-isoglutamine, Pam3CSK4, quil A and trehalose dimycolate.

As used herein, the term "administering" means providing a pharmaceutical agent or composition to a subject, and includes, but is not limited to, administering by a medical professional and self-administering. Such an agent can contain, for example, peptide described herein, an antigen-presenting cell provided herein and/or a CTL provided herein. The term "biological sample," "tissue sample," or simply "sample" each refers to a collection of cells obtained from a tissue of a subject. The source of the tissue sample may be solid tissue, as from a fresh, frozen and/or preserved organ, tissue sample, biopsy, or aspirate; blood or any blood constituents, serum, blood; bodily fluids such as cerebral spinal fluid, amniotic fluid, peritoneal fluid or interstitial fluid, urine, saliva, stool, tears; or cells from any time in gestation or development of the subject.

The term "binding" or "interacting" refers to an association, which may be a stable association, between two molecules, e.g., between a T cell receptor (TCR) and a peptide/MHC, due to, for example, electrostatic, hydrophobic, ionic and/or hydrogen-bond interactions under physiological conditions.

As used herein, the term "cancer" includes, but is not limited to, solid tumors and blood borne tumors. The term cancer includes diseases of the skin, tissues, organs, bone, cartilage, blood and vessels. The term "cancer" further encompasses primary and metastatic cancers.

The term "epitope" means a protein determinant capable of specific binding to an antibody. Epitopes usually consist of chemically active surface groupings of molecules such as amino acids or sugar side chains. Certain epitopes can be defined by a particular sequence of amino acids to which a T cell receptor or antibody is capable of binding.

As used herein, the phrase "pharmaceutically acceptable" refers to those agents, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions (21) polyesters, polycarbonates and/or polyanhydrides; and (22) other non-toxic compatible substances employed in pharmaceutical formulations.

As used herein, a therapeutic that "prevents" a condition refers to a compound that, when administered to a statistical sample prior to the onset of the disorder or condition, reduces the occurrence of the disorder or condition in the treated sample relative to an untreated control sample, or delays the onset or reduces the severity of one or more symptoms of the disorder or condition relative to the untreated control sample. As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

T Cells

In certain aspects, provided herein are methods related to selecting T cells (e.g., CD8 T cells, such as CTLs and/or CD4 T cells) or a sample comprising T cells (e.g., CD8 T cells, such as CTLs and/or CD4 T cells) for adoptive immunotherapy, for expansion and/or for inclusion in a cell bank, e.g., by determining the expression of a biomarker (e.g., IFNg, IL-2, TNF, GzmB, GzmK. Prf, CD8, CD4, PD-1, TIM-3, LAG-3, CTLA-4 and/or antigen-specific TCR) in the total lymphocytes, T cells, CD8 T cells and/or CD4 T cells and selecting the sample for adoptive immunotherapy, expansion or inclusion into a cell bank if at least a threshold portion of the total lymphocytes, T cells, CD8 T cells and/or CD4 T cells in the sample express one or more of the biomarkers.

In certain aspects, also provided herein are methods related to selecting a subject for adoptive immunotherapy or to provide a sample comprising T cells (e.g., for inclusion in a cell bank or use in adoptive therapy) by obtaining a sample comprising T cells from the subject and determining the expression of a biomarker (e.g., IFNg, IL-2, TNF, GzmB, GzmK, Prf, CD8, CD4, PD-1, TIM-3, LAG-3, CTLA-4 and/or antigen-specific TCR) in the total lymphocytes, T cells, CD8 T cells and/or CD4 T cells in the sample and selecting the subject for adoptive immunotherapy or to provide a sample if at least a threshold portion of the total lymphocytes, T cells, CD8 T cells and/or CD4 T cells in the sample express the biomarker. In some embodiments, the T cell is a cytotoxic T lymphocyte (CTL).

In certain embodiments, the method includes determining the expression of CD107a in the sample and selecting the sample or subject if at least a threshold portion of the total lymphocytes, T cells, CD8 T cells and/or CD4 T cells in the sample express CD107a. In certain embodiments, the method includes determining the expression of IFNg in the sample and selecting the sample or subject if at least a threshold portion of the total lymphocytes, T cells, CD8 T cells and/or CD4 T cells in the sample express IFNg. In certain embodiments, the method includes determining the expression of IL-2 in the sample and selecting the sample or subject if at least a threshold portion of the total lymphocytes, T cells, CD8 T cells and/or CD4 T cells in the sample express IL-2. In certain embodiments, the method includes determining the expression of TNF in the sample and selecting the sample or subject if at least a threshold portion of the total lymphocytes. T cells, CD8 T cells and/or CD4 T cells in the sample express TNF. In certain embodiments, the method includes determining the expression of granzyme B in the sample and selecting the sample or subject if at least a threshold portion of the total lymphocytes, T cells, CD8 T cells and/or CD4 T cells in the sample express granzyme B. In certain embodiments, the method includes determining the expression of granzyme K in the sample and selecting the sample or subject if at least a threshold portion of the total lymphocytes. T cells, CD8 T cells and/or CD4 T cells in the sample express granzyme K. In certain embodiments, the method includes determining the expression of perforin in the sample and selecting the sample or subject if at least a threshold portion of the total lymphocytes, T cells, CD8 T cells and/or CD4 T cells in the sample express perforin.

In certain embodiments, the method includes determining the expression of CD107a and IFNg in the sample and selecting the sample or subject if at least a threshold portion of the total lymphocytes, T cells, CD8 T cells and/or CD4 T cells in the sample express CD107a and IFNg. In certain embodiments, the method includes determining the expression of CD107a and IL-2 in the sample and selecting the sample or subject if at least a threshold portion of the total lymphocytes, T cells, CD8 T cells and/or CD4 T cells in the sample express CD107a and IL-2. In certain embodiments, the method includes determining the expression of CD107a and TNF in the sample and selecting the sample or subject if at least a threshold portion of the total lymphocytes, T cells, CD8 T cells and/or CD4 T cells in the sample express CD107a and TNF. In certain embodiments, the method includes determining the expression of IL-2 and TNF in the sample and selecting the sample or subject if at least a threshold portion of the total lymphocytes, T cells, CD8 T cells and/or CD4 T cells in the sample express IL-2 and TNF. In certain embodiments, the method includes determining the expression of IFNg and TNF in the sample and selecting the sample or subject if at least a threshold portion of the total lymphocytes, T cells, CD8 T cells and/or CD4 T cells in the sample express IFNg and TNF. In certain embodiments, the method includes determining the expression of IL-2 and IFNg in the sample and selecting the sample or subject if at least a threshold portion of the total lymphocytes. T cells, CD8 T cells and/or CD4 T cells in the sample express IL-2 and IFNg.

In certain embodiments, the method includes determining the expression of CD107a and granzyme B in the sample and selecting the sample or subject if at least a threshold portion of the total lymphocytes, T cells, CD8 T cells and/or CD4 T cells in the sample express CD107a and granzyme B. In certain embodiments, the method includes determining the expression of CD107a and granzyme K in the sample and selecting the sample or subject if at least a threshold portion of the total lymphocytes, T cells, CD8 T cells and/or CD4 T cells in the sample express CD107a and granzyme K. In certain embodiments, the method includes determining the expression of CD107a and perforin in the sample and selecting the sample or subject if at least a threshold portion of the total lymphocytes, T cells, CD8 T cells and/or CD4 T cells in the sample express CD107a and perforin. In certain embodiments, the method includes determining the expression of IL-2 and granzyme K in the sample and selecting the sample or subject if at least a threshold portion of the total lymphocytes, T cells, CD8 T cells and/or CD4 T cells in the sample express IL-2 and granzyme K. In certain embodiments, the method includes determining the expression of IL-2 and granzyme B in the sample and selecting the sample or subject if at least a threshold portion of the total lymphocytes, T cells, CD8 T cells and/or CD4 T cells in the sample express IL-2 and granzyme B. In certain embodiments, the method includes determining the expression of IL-2 and perforin in the sample and selecting the sample or subject if at least a threshold portion of the total lymphocytes, T cells, CD8 T cells and/or CD4 T cells in the sample express IL-2 and perforin. In certain embodiments, the method includes determining the expression of IFNg and granzyme B in the sample and selecting the sample or subject if at least a threshold portion of the total lymphocytes, T cells, CD8 T cells and/or CD4 T cells in the sample express IFNg and granzyme B. In certain embodiments, the method includes determining the expression of IFNg and granzyme K in the sample and selecting the sample or subject if at least a threshold portion of the total lymphocytes, T cells, CD8 T cells and/or CD4 T cells in the sample express IFNg and granzyme K. In certain embodiments, the method includes determining the expression of IFNg and perforin in the sample and selecting the sample or subject if at least a threshold portion of the total lymphocytes. T cells, CD8 T cells and/or CD4 T cells in the sample express IFNg and perforin. In certain embodiments, the method includes determining the expression of TNF and granzyme B in the sample and selecting the sample or subject if at least a threshold portion of the total lymphocytes, T cells, CD8 T cells and/or CD4 T cells in the sample express TNF and granzyme B. In certain embodiments, the method includes determining the expression of TNF and granzyme K in the sample and selecting the sample or subject if at least a threshold portion of the total lymphocytes, T cells, CD8 T cells and/or CD4 T cells in the sample express TNF and granzyme K. In certain embodiments, the method includes determining the expression of TNF and perforin in the sample and selecting the sample or subject if at least a threshold portion of the total lymphocytes, T cells, CD8 T cells and/or CD4 T cells in the sample express TNF and perforin.

In certain embodiments, the method includes determining the expression of granzyme B and granzyme K in the sample and selecting the sample or subject if at least a threshold portion of the total lymphocytes, T cells, CD8 T cells and/or CD4 T cells in the sample express granzyme B and granzyme K. In certain embodiments, the method includes determining the expression of perforin and granzyme K in the sample and selecting the sample or subject if at least a threshold portion of the total lymphocytes, T cells, CD8 T cells and/or CD4 T cells in the sample express perforin and granzyme K. In certain embodiments, the method includes determining the expression of granzyme B and perforin in the sample and selecting the sample or subject if at least a threshold portion of the total lymphocytes, T cells, CD8 T cells and/or CD4 T cells in the sample express granzyme B and perforin.

In certain embodiments, the method includes determining the expression of CD107a, IL-2, and IFNg in the sample and selecting the sample or subject if at least a threshold portion of the total lymphocytes, T cells, CD8 T cells and/or CD4 T cells in the sample express CD107a, IL-2, and IFNg.

In certain embodiments, the method includes determining the expression of CD107a, TNF, and IFNg in the sample and selecting the sample or subject if at least a threshold portion of the total lymphocytes, T cells, CD8 T cells and/or CD4 T cells in the sample express CD107a, TNF, and IFNg.

In certain embodiments, the method includes determining the expression of IL-2, TNF, and IFNg in the sample and selecting the sample or subject if at least a threshold portion of the total lymphocytes, T cells, CD8 T cells and/or CD4 T cells in the sample express IL-2, TNF, and IFNg.

In certain embodiments, the method includes determining the expression of CD107a, IL-2, and granzyme B in the sample and selecting the sample or subject if at least a threshold portion of the total lymphocytes, T cells, CD8 T cells and/or CD4 T cells in the sample express CD107a, IL-2, and granzyme B.

In certain embodiments, the method includes determining the expression of CD107a, IL-2, and granzyme K in the sample and selecting the sample or subject if at least a threshold portion of the total lymphocytes, T cells, CD8 T cells and/or CD4 T cells in the sample express CD107a, IL-2, and granzyme K.

In certain embodiments, the method includes determining the expression of CD107a, IL-2, and perforin in the sample and selecting the sample or subject if at least a threshold portion of the total lymphocytes, T cells, CD8 T cells and/or CD4 T cells in the sample express CD107a, IL-2, and perforin.

In certain embodiments, the method includes determining the expression of CD107a, TNF, and granzyme B in the sample and selecting the sample or subject if at least a threshold portion of the total lymphocytes, T cells, CD8 T cells and/or CD4 T cells in the sample express CD107a, TNF, and granzyme B.

In certain embodiments, the method includes determining the expression of CD107a, TNF, and granzyme K in the sample and selecting the sample or subject if at least a threshold portion of the total lymphocytes, T cells, CD8 T cells and/or CD4 T cells in the sample express CD107a, TNF, and granzyme K.

In certain embodiments, the method includes determining the expression of CD107a, TNF, and perforin in the sample and selecting the sample or subject if at least a threshold portion of the total lymphocytes, T cells, CD8 T cells and/or CD4 T cells in the sample express CD107a, TNF, and perforin.

In certain embodiments, the method includes determining the expression of CD107a, IFNg, and granzyme B in the sample and selecting the sample or subject if at least a threshold portion of the total lymphocytes, T cells, CD8 T cells and/or CD4 T cells in the sample express IFNg, IL-2, and granzyme B.

In certain embodiments, the method includes determining the expression of CD107a, IFNg, and granzyme K in the sample and selecting the sample or subject if at least a threshold portion of the total lymphocytes, T cells, CD8 T cells and/or CD4 T cells in the sample express IFNg, IL-2, and granzyme K.

In certain embodiments, the method includes determining the expression of CD107a, IFNg, and perforin in the sample and selecting the sample or subject if at least a threshold portion of the total lymphocytes, T cells, CD8 T cells and/or CD4 T cells in the sample express IFNg, IL-2, and perforin.

In certain embodiments, the method includes determining the expression of IL-2, TNF, and granzyme B in the sample and selecting the sample or subject if at least a threshold portion of the total lymphocytes, T cells, CD8 T cells and/or CD4 T cells in the sample express IL-2, TNF, and granzyme B.

In certain embodiments, the method includes determining the expression of IL-2, TNF, and granzyme K in the sample and selecting the sample or subject if at least a threshold portion of the total lymphocytes, T cells, CD8 T cells and/or CD4 T cells in the sample express IL-2, TNF, and granzyme K.

In certain embodiments, the method includes determining the expression of IL-2, TNF, and perforin in the sample and selecting the sample or subject if at least a threshold portion of the total lymphocytes, T cells, CD8 T cells and/or CD4 T cells in the sample express IFNg. TNF, and perforin.

In certain embodiments, the method includes determining the expression of IFNg, TNF, and granzyme B in the sample and selecting the sample or subject if at least a threshold portion of the total lymphocytes, T cells, CD8 T cells and/or CD4 T cells in the sample express IFNg, TNF, and granzyme B.

In certain embodiments, the method includes determining the expression of IFNg, TNF, and granzyme K in the sample and selecting the sample or subject if at least a threshold portion of the total lymphocytes, T cells, CD8 T cells and/or CD4 T cells in the sample express IFNg, TNF, and granzyme K.

In certain embodiments, the method includes determining the expression of IFNg, TNF, and perforin in the sample and selecting the sample or subject if at least a threshold portion of the total lymphocytes, T cells, CD8 T cells and/or CD4 T cells in the sample express IFNg, TNF, and perforin.

In certain embodiments, the method includes determining the expression of IL-2, TNF, and IFNg in the sample and selecting the sample or subject if at least a threshold portion of the total lymphocytes, T cells, CD8 T cells and/or CD4 T cells in the sample express IL-2, TNF, and IFNg.

In certain embodiments, the method includes determining the expression of granzyme K, granzyme B, and/or perforin in the sample and selecting the sample or subject if at least a threshold portion of the total lymphocytes, T cells, CD8 T cells and/or CD4 T cells in the sample express granzyme K, granzyme B, and/or perforin.

In certain embodiments, the method includes determining the expression of CD107a, IL-2, TNF, and IFNg in the sample and selecting the sample or subject if at least a threshold portion of the total lymphocytes, T cells, CD8 T cells and/or CD4 T cells in the sample express CD107a, IL-2, TNF, and IFNg.

In certain embodiments, the method includes determining the expression of CD107a, IL-2, TNF, and granzyme B in the sample and selecting the sample or subject if at least a threshold portion of the total lymphocytes, T cells, CD8 T cells and/or CD4 T cells in the sample express CD107a, IL-2, TNF, and granzyme B.

In certain embodiments, the method includes determining the expression of CD107a, IL-2, TNF, and granzyme K in the sample and selecting the sample or subject if at least a threshold portion of the total lymphocytes, T cells, CD8 T cells and/or CD4 T cells in the sample express CD107a, IL-2, TNF, and granzyme K.

In certain embodiments, the method includes determining the expression of CD107a, IL-2, TNF, and perforin in the sample and selecting the sample or subject if at least a threshold portion of the total lymphocytes, T cells, CD8 T cells and/or CD4 T cells in the sample express CD107a, IL-2, TNF, and perforin.

In certain embodiments, the method includes determining the expression of CD107a, IL-2, IFNg, and granzyme B in the sample and selecting the sample or subject if at least a threshold portion of the total lymphocytes, T cells, CD8 T cells and/or CD4 T cells in the sample express CD107a, IL-2, IFNg, and granzyme B.

In certain embodiments, the method includes determining the expression of CD107a, IL-2, IFNg, and granzyme K in the sample and selecting the sample or subject if at least a threshold portion of the total lymphocytes, T cells, CD8 T cells and/or CD4 T cells in the sample express CD107a, IL-2, IFNg, and granzyme K.

In certain embodiments, the method includes determining the expression of CD107a, IL-2, IFNg, and perforin in the sample and selecting the sample or subject if at least a threshold portion of the total lymphocytes, T cells, CD8 T cells and/or CD4 T cells in the sample express CD107a, IL-2, IFNg, and perforin.

In certain embodiments, the method includes determining the expression of TNF, IL-2, IFNg, and granzyme B in the sample and selecting the sample or subject if at least a threshold portion of the total lymphocytes, T cells, CD8 T cells and/or CD4 T cells in the sample express TNF, IL-2, IFNg, and granzyme B.

In certain embodiments, the method includes determining the expression of TNF, IL-2, IFNg, and granzyme K in the sample and selecting the sample or subject if at least a threshold portion of the total lymphocytes, T cells, CD8 T cells and/or CD4 T cells in the sample express TNF, IL-2, IFNg, and granzyme K.

In certain embodiments, the method includes determining the expression of TNF, IL-2, IFNg, and perforin in the sample and selecting the sample or subject if at least a threshold portion of the total lymphocytes, T cells, CD8 T cells and/or CD4 T cells in the sample express TNF, IL-2, IFNg, and perforin.

In certain embodiments, the method includes determining the expression of TNF, granzyme K, granzyme B, and perforin in the sample and selecting the sample or subject if at least a threshold portion of the total lymphocytes, T cells, CD8 T cells and/or CD4 T cells in the sample express TNF, granzyme K, granzyme B, and perforin.

In certain embodiments, the method includes determining the expression of CD107a, granzyme K, granzyme B, and perforin in the sample and selecting the sample or subject if at least a threshold portion of the total lymphocytes, T cells, CD8 T cells and/or CD4 T cells in the sample express CD107a, granzyme K, granzyme B, and perforin.

In certain embodiments, the method includes determining the expression of IFNg, granzyme K, granzyme B, and perforin in the sample and selecting the sample or subject if at least a threshold portion of the total lymphocytes, T cells, CD8 T cells and/or CD4 T cells in the sample express IFNg, granzyme K, granzyme B, and perforin.

In certain embodiments, the method includes determining the expression of IL-2, granzyme K, granzyme B, and perforin in the sample and selecting the sample or subject if at least a threshold portion of the total lymphocytes, T cells, CD8 T cells and/or CD4 T cells in the sample express IL-2, granzyme K, granzyme B, and perforin.

In certain embodiments, the method includes determining the expression of TNF, CD107a, granzyme K, granzyme B, and perforin in the sample and selecting the sample or subject if at least a threshold portion of the total lymphocytes, T cells, CD8 T cells and/or CD4 T cells in the sample express TNF, CD107a, granzyme K, granzyme B, and perforin.

In certain embodiments, the method includes determining the expression of TNF, IFNg, granzyme K, granzyme B, and perforin in the sample and selecting the sample or subject if at least a threshold portion of the total lymphocytes, T cells, CD8 T cells and/or CD4 T cells in the sample express TNF, IFNg, granzyme K, granzyme B, and perforin.

In certain embodiments, the method includes determining the expression of TNF, IL-2, granzyme K, granzyme B, and perforin in the sample and selecting the sample or subject if at least a threshold portion of the total lymphocytes, T cells, CD8 T cells and/or CD4 T cells in the sample express TNF, IL-2, granzyme K, granzyme B, and perforin.

In certain embodiments, the method includes determining the expression of IL-2, CD107a, granzyme K, granzyme B, and perforin in the sample and selecting the sample or subject if at least a threshold portion of the total lymphocytes, T cells, CD8 T cells and/or CD4 T cells in the sample express IL-2, CD107a, granzyme K, granzyme B, and perforin.

In certain embodiments, the method includes determining the expression of IFNg, CD107a, granzyme K, granzyme B, and perforin in the sample and selecting the sample or subject if at least a threshold portion of the total lymphocytes, T cells, CD8 T cells and/or CD4 T cells in the sample express IFNg, CD107a, granzyme K, granzyme B, and perforin.

In certain embodiments, the method includes determining the expression of IFNg. IL-2, granzyme K, granzyme B, and perforin in the sample and selecting the sample or subject if at least a threshold portion of the total lymphocytes, T cells, CD8 T cells and/or CD4 T cells in the sample express IFNg, IL-2, granzyme K, granzyme B, and perforin.

In certain embodiments, the method includes determining the expression of IL-2, CD107a, TNF, granzyme B, and perforin in the sample and selecting the sample or subject if at least a threshold portion of the total lymphocytes, T cells, CD8 T cells and/or CD4 T cells in the sample express IL-2, CD107a, TNF, granzyme B, and perforin.

In certain embodiments, the method includes determining the expression of IFNg, CD107a, TNF, granzyme B, and perforin in the sample and selecting the sample or subject if at least a threshold portion of the total lymphocytes, T cells, CD8 T cells and/or CD4 T cells in the sample express IFNg, CD107a, TNF, granzyme B, and perforin.

In certain embodiments, the method includes determining the expression of IL-2, CD107a, TNF, granzyme K, and perforin in the sample and selecting the sample or subject if at least a threshold portion of the total lymphocytes, T cells, CD8 T cells and/or CD4 T cells in the sample express IL-2, CD107a, TNF, granzyme K, and perforin.

In certain embodiments, the method includes determining the expression of IFNg, CD107a, TNF, granzyme K, and perforin in the sample and selecting the sample or subject if at least a threshold portion of the total lymphocytes. T cells, CD8 T cells and/or CD4 T cells in the sample express IFNg, CD107a, TNF, granzyme K, and perforin.

In certain embodiments, the method includes determining the expression of IL-2, CD107a, TNF, granzyme K, and perforin in the sample and selecting the sample or subject if at least a threshold portion of the total lymphocytes, T cells, CD8 T cells and/or CD4 T cells in the sample express IL-2, CD107a, TNF, granzyme K, and granzyme B.

In certain embodiments, the method includes determining the expression of IFNg, CD107a, TNF, granzyme K, and perforin in the sample and selecting the sample or subject if at least a threshold portion of the total lymphocytes, T cells, CD8 T cells and/or CD4 T cells in the sample express IFNg, CD107a, TNF, granzyme K, and granzyme B.

In certain embodiments, the method includes determining the expression of IL-2, IFNg, TNF, granzyme K, and granzyme B in the sample and selecting the sample or subject if at least a threshold portion of the total lymphocytes, T cells, CD8 T cells and/or CD4 T cells in the sample express IL-2, IFNg, TNF, granzyme K, and granzyme B.

In certain embodiments, the method includes determining the expression of IFNg, CD107a, TNF, granzyme K, granzyme B, and perforin in the sample and selecting the sample or subject if at least a threshold portion of the total lymphocytes, T cells, CD8 T cells and/or CD4 T cells in the sample express IFNg, CD107a, TNF, granzyme K, granzyme B, and perforin.

In certain embodiments, the method includes determining the expression of IL-2, CD107a, TNF, granzyme K, granzyme B, and perforin in the sample and selecting the sample or subject if at least a threshold portion of the total lymphocytes, T cells, CD8 T cells and/or CD4 T cells in the sample express IL-2, CD107a. TNF, granzyme K, granzyme B, and perforin.

In certain embodiments, the method includes determining the expression of IL-2, IFNg, TNF, granzyme K, granzyme B, and perforin in the sample and selecting the sample or subject if at least a threshold portion of the total lymphocytes, T cells, CD8 T cells and/or CD4 T cells in the sample express IL-2, IFNg TNF, granzyme K, granzyme B, and perforin.

In certain embodiments, the method includes determining the expression of IL-2, CD107a, TNF, IFNg, granzyme B, and perforin in the sample and selecting the sample or subject if at least a threshold portion of the total lymphocytes, T cells, CD8 T cells and/or CD4 T cells in the sample express IL-2, CD107a, TNF, IFNg, granzyme B, and perforin.

In certain embodiments, the method includes determining the expression of IL-2, CD107a, TNF, IFNg, granzyme K, and perforin in the sample and selecting the sample or subject if at least a threshold portion of the total lymphocytes, T cells, CD8 T cells and/or CD4 T cells in the sample express IL-2, CD107a, TNF, IFNg, granzyme K, and perforin.

In certain embodiments, the method includes determining the expression of IL-2, CD107a, TNF, IFNg, granzyme K, and granzyme B in the sample and selecting the sample or subject if at least a threshold portion of the total lymphocytes, T cells, CD8 T cells and/or CD4 T cells in the sample express IL-2, CD107a, TNF, IFNg, granzyme K, and granzyme B.

In certain embodiments, the method includes determining the expression of IL-2, CD107a, TNF, IFNg, granzyme K, perforin, and granzyme B in the sample and selecting the sample or subject if at least a threshold portion of the total lymphocytes, T cells, CD8 T cells and/or CD4 T cells in the sample express IL-2, CD107a, TNF, IFNg, perforin, granzyme K, and granzyme B.

In certain embodiments, the threshold level of the total lymphocytes, T cells, CD8 T cells and/or CD4 T cells expressing CD107a in a sample is met if at least 0.5%, 0.6%, 0.7%, 0.8%, 0.9%, 1.0%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the total lymphocytes, T cells, CD8 T cells and/or CD4 T cells in the sample express CD107a.

In certain embodiments, the threshold level of the total lymphocytes, T cells, CD8 T cells and/or CD4 T cells expressing IFNg in a sample is met if at least 0.5%, 0.6%, 0.7%, 0.8%, 0.9%, 1.0%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the total lymphocytes, T cells, CD8 T cells and/or CD4 T cells in the sample express IFNg.

In certain embodiments, the threshold level of the total lymphocytes, T cells, CD8 T cells and/or CD4 T cells expressing IL-2 in a sample is met if at least 0.5%, 0.6%, 0.7%, 0.8%, 0.9%, 1.0%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the total lymphocytes, T cells, CD8 T cells and/or CD4 T cells in the sample express IL-2.

In certain embodiments, the threshold level of the total lymphocytes, T cells. CD8 T cells and/or CD4 T cells expressing TNF in a sample is met if at least 0.5%, 0.6%, 0.7%, 0.8%, 0.9%, 1.0%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the total lymphocytes, T cells, CD8 T cells and/or CD4 T cells in the sample express TNF.

In some embodiments, the threshold level of the total lymphocytes. T cells, CD8 T cells and/or CD4 T cells expressing CD107a in a sample is not met if less than 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% of the total lymphocytes, T cells, CD8 T cells and/or CD4 T cells in the sample express CD107a.

In some embodiments, the threshold level of the total lymphocytes, T cells, CD8 T cells and/or CD4 T cells expressing IFNg in a sample is not met if less than 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% of the total lymphocytes, T cells, CD8 T cells and/or CD4 T cells in the sample express IFNg.

In some embodiments, the threshold level of the total lymphocytes, T cells, CD8 T cells and/or CD4 T cells expressing IL-2 in a sample is not met if less than 15%, 14%, 13%, 12%, 11%, 10%, 9%, 8%, 7%, 6%, 4%, 3%, 2%, %/1%, 0.9%, 0.8%, 0.7%, 0.6%, 0.5%, 0.4%, 0.3%, 0.2%, or 0.1% of the total lymphocytes, T cells, CD8 T cells and/or CD4 T cells in the sample express IL-2.

In some embodiments, the threshold level of the total lymphocytes, T cells, CD8 T cells and/or CD4 T cells expressing TNF in a sample is not met if less than 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% of the total lymphocytes, T cells, CD8 T cells and/or CD4 T cells in the sample express TNF. In some embodiments, the threshold level of the total lymphocytes, T cells, CD8 T cells and/or CD4 T cells expressing granzyme B in a sample is met if at least 5%, 6%, 7%, 8%, 9%, 10%, 11% 12%, 13%, 14%, 15%, 16%, 17%, 18%, 19%, 20%, 21%, 22%, 23%, 24% or 25% of the lymphocytes in the sample express granzyme B.

In some embodiments, the threshold level of the total lymphocytes, T cells, CD8 T cells and/or CD4 T cells expressing granzyme K in a sample is met if at least 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells in the sample express granzyme K.

In some embodiments, the threshold level of the total lymphocytes, T cells, CD8 T cells and/or CD4 T cells expressing perforin a sample is met if at least 2%, 3%, 4%, 5%, 6%, 7%, 8%, 9%, 10%, 11%, 12%, 13%, 14% or 15% of the total lymphocytes. T cells, CD8 T cells and/or CD4 T cells in the sample express perforin.

In some embodiments, the threshold level of the total lymphocytes, T cells, CD8 T cells and/or CD4 T cells expressing granzyme B in a sample is not met if less than 5%, 6%, 7%, 8%, 9%, 10%, 11%, 12%, 13%, 14%, 15%, 16%, 17%, 18%, 19%, 20%, 21%, 22%, 23%, 24% or 25% of the total lymphocytes, T cells, CD8 T cells and/or CD4 T cells in the sample express granzyme B.

In some embodiments, the threshold level of the total lymphocytes, T cells, CD8 T cells and/or CD4 T cells expressing granzyme K in a sample is not met if less than 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells in the sample express granzyme K.

In some embodiments, the threshold level of the total lymphocytes, T cells, CD8 T cells and/or CD4 T cells expressing perforin a sample is not met if less than 2%, 3%, 4%, 5%, 6%, 7%, 8%, 9%, 10%, 11%, 12%, 13%, 14% or 15% of the total lymphocytes, T cells, CD8 T cells and/or CD4 T cells in the sample express perforin.

In some embodiments, the method further comprises determining the expression of CD8, CD4, PD-1, TIM-3, LAG-3 and/or CTLA-4 in the sample and selecting the sample or subject if at least a threshold portion of the total lymphocytes, T cells, CD8 T cells and/or CD4 T cells in the sample express granzyme B, granzyme K perforin, CD8, CD4, PD-1, TIM-3, LAG-3 and/or CTLA-4.

In some embodiments, the threshold level of the total lymphocytes expressing CD8 in a sample is met if at least 15%, 16%, 17%, 18%, 19%, 20%, 21%, 22%, 23%, 24%, 25%, 26%, 27%, 28%, 29% or 30% of the lymphocytes in the sample express CD8.

In certain embodiments, the threshold level of total lymphocytes expressing CD4 in a sample is met if at least 0.5%, 0.6%, 0.7%, 0.8%, 0.9%, 1.0%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91% 92%, 93%, 94%, 95%, 96%, 97%, 98%, 99% or 100% of the lymphocytes in the sample express CD4.

In some embodiments, the threshold level of the total lymphocytes, T cells, CD8 T cells and/or CD4 T cells expressing PD-1 in a sample is met if at least 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells in the sample express PD-1.

In some embodiments, the threshold level of the total lymphocytes, T cells, CD8 T cells and/or CD4 T cells expressing TIM-3 in a sample is met if at least 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells in the sample express TIM-3.

In some embodiments, the threshold level of the total lymphocytes, T cells, CD8 T cells and/or CD4 T cells expressing LAG-3 in a sample is met if at least 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells in the sample express LAG-3.

In some embodiments, the threshold level of the total lymphocytes, T cells, CD8 T cells and/or CD4 T cells expressing CTLA4 in a sample is met if at least 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells in the sample express CTLA-4.

In some embodiments, the threshold level of the total lymphocytes expressing CD8 in a sample is not met if less than 15%, 16%, 17%, 18%, 19%, 20%, 21%, 22%, 23%, 24%, 25%, 26%, 27%, 28%, 29% or 30% of the total lymphocytes in the sample express CD8.

In certain embodiments, the threshold level of the total lymphocytes expressing CD4 in a sample is not met if less than 1%, 2%, 3%, 4%, 5%, 6%, 7%, 8%, 9%, 10%, 1%, 12%, 13%, 14% 15%, 16%, 17%, 18%, 19%, 20%, 21%, 22%, 23%, 24%, 25%, 26%, 27%, 28%, 29% or 30% of the total lymphocytes in the sample express CD4.

In some embodiments, the threshold level of the total lymphocytes. T cells, CD8 T cells and/or CD4 T cells expressing PD-1 in a sample is not met if less than 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells in the sample express PD-1.

In some embodiments, the threshold level of the total lymphocytes, T cells, CD8 T cells and/or CD4 T cells expressing TIM-3 in a sample is not met if less than 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells in the sample express TIM-3.

In some embodiments, the threshold level of the total lymphocytes, T cells, CD8 T cells and/or CD4 T cells expressing LAG-3 in a sample is not met if less than 3%, 4%, 5%, 6%, 7%, 8%, 9%, 10%, 11%, 12%, 13%, 14%, 15%, 16%, 17%, 18%, 19% or 20% of the total lymphocytes, T cells, CD8 T cells and/or CD4 T cells in the sample express LAG-3.

In some embodiments, the threshold level of the total lymphocytes, T cells, CD8 T cells and/or CD4 T cells expressing CTLA-4 in a sample is not met if less than 3%, 4%, 5%, 6%, 7% 8%, 9%, 10%, 11%, 12%, 13%, 14%, 15%, 16%, 17%, 18%, 19% or 20% of the total lymphocytes, T cells, CD8 T cells and/or CD4 T cells in the sample express CTLA-4.

In some embodiments, the T cells (e.g., CD8 and/or CD4 T cells) provided herein express a T cell receptor that specifically binds to a peptide presented on an MHC (e.g., a class I MHC and/or a class II MHC). In some embodiments, the MHC is a class I MHC. In some embodiments, the class I MHC has an α chain polypeptide that is HLA-A, HLA-B, HLA-C, HLA-E, HLA-F, HLA-g, HLA-K or HLA-L. In some embodiments, the peptide is a peptide described herein. In some embodiments, the T cells in the sample express a TCR specific for an Epstein-Barr Virus (EBV) peptide (e.g., a LMP1 peptide, a LMP2A peptide or an EBNA1 peptide) presented on a class I MHC. In some embodiments, the T cells express one or more EBV peptides or fragments thereof.

In some embodiments, any assay capable of detecting expression of the relevant biomarker can be used in the methods provided herein. In some embodiments, the biomarkers are detected using fluorescence activated cell sorting (FACS). In some embodiments, the biomarkers are detected using ELISpot. In some embodiments, the biomarkers are detected using microscopy (e.g., fluorescence microscopy).

T cells described herein may be generated, activated (e.g., prior to selection) by inducing peptide-specific T cell proliferation and/or activation by incubating a sample comprising T cells with the antigen-presenting cells (APCs), thereby inducing the T cells to proliferate. In some embodiments, the APCs that present a peptide described herein (e.g., a peptide comprising one or more LMP1, LMP2A, or EBNA1 epitope sequences). In some embodiments the APCs are B cells, antigen-presenting T-cells, dendritic cells, or artificial antigen-presenting cells (e.g., aK562 cells).

Dendritic cells for use in the process may be prepared by taking peripheral blood mononuclear cells (PBMCs) from a patient sample and adhering them to plastic. Generally the monocyte population sticks and all other cells can be washed off. The adherent population is then differentiated with IL-4 and GM-CSF to produce monocyte derived dendritic cells. These cells may be matured by the addition of IL-1β, IL-6, PGE-1 and TNF-α (which upregulates the important co-stimulatory molecules on the surface of the dendritic cell) and are then transduced with one or more of the peptides provided herein.

APCs that present the one or more of peptides described herein may be generated by contacting an APC with a peptide comprising a T cell epitope and/or with a nucleic acid encoding a peptide comprising a T cell epitope. In some embodiments, the APCs are irradiated. In some embodiments, the APCs that present a peptide described herein (e.g., a peptide comprising one or more LMP1, LMP2A, or EBNA1 epitope sequences). A cell presenting a peptide described herein can be produced by standard techniques known in the art. For example, a cell may be pulsed to encourage peptide uptake. In some embodiments, the cells are transfected with a nucleic acid encoding a peptide provided herein. Provided herein are methods of producing antigen-presenting cells (APCs), comprising pulsing a cell with the peptides described herein. Exemplary examples of producing antigen-presenting cells can be found in WO2013088114, hereby incorporated in its entirety.

In some embodiments, the methods provided herein include steps of generating, activating and/or inducing proliferation of T cells (e.g., CTLs, CD8 T cells, and/or CD4 T cells) that recognize one or more of the T cell (e.g., CTL) epitopes described herein prior to selection. In some embodiments, a sample comprising T cells (i.e., a PBMC sample) is incubated in culture with an APC provided herein (e.g., an APC that presents a peptide comprising a T cell epitope on a class I MHC complex). In some embodiments, the APCs are autologous to the subject from whom the T cells were obtained. In some embodiments, the APCs are not autologous (i.e., allogeneic) to the subject from whom the T cells were obtained. In some embodiments, the sample containing T cells are incubated 2 or more times with APCs provided herein. In some embodiments, the T cells are incubated with the APCs in the presence of at least one cytokine. In some embodiments, the cytokine is IL-4, IL-7 and/or IL-15. Exemplary methods for inducing proliferation of T cells using APCs are provided, for example, in U.S. Pat. Pub. No. 2015/0017723, which is hereby incorporated by reference.

In some aspects, provided herein are methods comprising the administration of samples and/or T cells (e.g., CTLs, CD8 T cells, and/or CD4 T cells) from selected according a method provided herein to a subject in order to treat and/or prevent a disease or disorder (e.g., cancer, an infectious disease and/or an autoimmune disorder). In some embodiments, the method includes administering to the subject an effective amount of the T cells provided herein. In some embodiments, the composition includes a combination of multiple (e.g., two or more) T cells (e.g., CD4 T cells or CD8 T cells, such as CTLs) provided herein. In some embodiments, the T cells are autologous to the subject. In some embodiments, the T cells are stored in a cell bank before they are administered to the subject.

Peptides

In some embodiments, the methods and compositions provided herein relate to peptide-specific T cells (e.g., CTLs, CD8 T cells, and/or CD4 T cells). In some embodiments, the methods include the generation of such T cells, for example, by incubating a sample comprising T cells (i.e., a PBMC sample) with antigen-presenting cells (APCs) that present one or more of the T cell epitopes described herein (e.g., APCs that present a peptide described herein comprising a CTL epitope on a class I MHC complex).

In some embodiments, the peptides provided herein comprise a sequence of any EBV viral protein (e.g., a sequence of at least 5, 6, 7, 8, 9, 10, 11, 12, 13, 14, 15, 16, 17, 18, 19 or 20 contiguous amino acids of any EBV protein). In some embodiments, the peptides provided herein comprise no more than 25, 20, 19, 18, 17, 16, 15, 14, 13, 12, 11 or 10 contiguous amino acids of the EBV viral protein.

In some embodiments, the peptides provided herein comprise a sequence of LMP1 (e.g., a sequence of at least 5, 6, 7, 8, 9, 10, 11, 12, 13, 14, 15, 16, 17, 18, 19 or 20 contiguous amino acids of LMP1). In some embodiments, the peptides provided herein comprise no more than 25, 20, 19, 18, 17, 16, 15, 14, 13, 12, 11 or 10 contiguous amino acids of LMP1. An exemplary LMP1 amino acid sequence is provided below (SEQ ID NO: 1):

```
  1  mdldlergpp gprrpprgpp lyysialall llllallfwl yiimsnwtgg allvlyafal 61  mlviiiliif ifrrdllcpl galclllmi tlllialwnl lgqalylgiv lfifgcllvl 121  giwvyfleil wrlgatiwql lafflaffld illliialyl qqnwwtllvd llwlllflai 181  liwmyyhgqr hsdehhhdds lphpqqatdd ssnhsdsnsn egrhhllvsg agdapplcsq 241  nlgapgggpd ngpqdpdntd dngpqdpdnt ddngphdplp qdpdntddng pqdpdntddn 301  gphdplphnp sdsagndggp pnlteevenk ggdrgppsmt dggggdphlp tlllgtsgsg 361  gddddphgpv qlsyyd
```

In some embodiments, the peptides provided herein comprise a sequence of LMP2A (e.g., a sequence of at least 5, 6, 7, 8, 9, 10, 11, 12, 13, 14, 15, 16, 17, 18, 19 or 20 contiguous amino acids of LMP2A). In some embodiments, the peptides provided herein comprise no more than 25, 20, 19, 18, 17, 16, 15, 14, 13, 12, 11 or 10 contiguous amino acids of LMP2A. An exemplary LMP2A amino acid sequence is provided below (SEQ ID NO: 2):

```
  1  mgslemvpmg agppspggdp dgddggnnsq ypsasgsdgn tptppndeer esneeppppy 61  edldwgngdr hsdyqplgnq dpslylglqh dgndglpppp ysprddssqh iyeeagrgsm 121  npvclpviva pylfwlaaia ascftasvst vvtatglals llllaavass yaaaqrkllt 181  pvtvltavvt ffaicltwri edppfnsllf allaaagglq giyvlvmlvl lilayrrrwr 241  rltvcggimf lacvlvlivd avlqlspllg avtvvsmtll llafvlwlss pgglgtlgaa 301  lltlaaalal laslilgtln lttmfllmll wtlvvllics scsscpltki llarlflyal 361  allllasali aggsilqtnf kslsstefip nlfcmllliv agilfilail tewgsgnrty 421  gpvfmclggl ltmvagavwl tvmtntllsa wiltagflif ligfalfgvi rccryccyyc 481  ltleseerpp tpyrntv
```

In some embodiments, the peptides provided herein comprise a sequence of EBNA1 (e.g., a sequence of at least 5, 6, 7, 8, 9, 10, 11, 12, 13, 14, 15, 16, 17, 18, 19 or 20 contiguous amino acids of EBNA1). In some embodiments, the peptides provided herein comprise no more than 25, 20, 19, 18, 17, 16, 15, 14, 13, 12, 11 or 10 contiguous amino acids of EBNA1. An exemplary EBNA1 amino acid sequence is provided below (SEQ ID NO: 3):

```
  1  pffhpvgead yfeylqeggp dgepdvppga ieqgpaddpg egpstgprgq gdggrrkkgg 61  wfgkhrgqgg snpkfeniae glrvllarsh vertteegtw vagvfvyggs ktslynlrrg 121  talaipqcrl tplsrlpfgm apgpgpqpgp lresivcyfm vflqthifae vlkdaikdlv 181  mtkpaptcni kvtvcsfddg vdlppwfppm vegaaaegdd gddgdeggdg degeegqe
```

In some embodiments, the peptide comprises the sequence of an epitope listed in Table 1.

TABLE 1

Exemplary EBV viral protein epitopes

| Peptide Sequence | HLA Restriction | SEQ ID No: |
|---|---|---|
| PYLFWLAAI | A*2301/A*2402/03 | 4 |
| SSCSSCPLSKI | A*1101 | 5 |
| TYGPVFMCL | A*2402 | 6 |
| RRRWRRLTV | B*27/02/04/05/06/09 | 7 |
| LLSAWILTA | A*0203 | 8 |
| LTAGFLIFL | A*0206 | 9 |
| CLGGLLTMV | A*0201 | 10 |
| VMSNTLLSAW | A*25/A*26 | 11 |
| MSNTLLSAW | B*58 | 12 |
| IEDPPFNSL | B*4001 | 13 |
| YLLEMLWRL | A*02 | 14 |
| YLQQNWWTL | A*02 | 15 |
| ALLVLYSFA | A*02 | 16 |
| IALYLQQNW | B*57/B*58 | 17 |
| FLYALALLL | A*0201 | 18 |
| WTLVVLLI | A*24 | 19 |
| CPLSKILL | B*0801 | 20 |
| HPVGEADYFEY | B*35 | 21 |
| RPQKRPSCI | B*0702 | 22 |
| IPQCRLTPL | B*0702 | 23 |
| LSRLPFGMA | B*5701 | 24 |
| YNLRRGTAL | B*0801 | 25 |
| VLKDAIKDL | A*0203 | 26 |
| FVYGGSKTSL | C*0303/C*0304 | 27 |
| FVYGGSKTSLY | A*26 | 28 |
| HPVGEADYF | B*53 | 29 |
| LQTHIFAEV | A*0206 | 30 |
| FMVFLQTHI | A*0201 | 31 |

In some embodiments, the peptides provided herein comprise two or more of the T cell epitopes (e.g., viral epitopes). In some embodiments, the peptides provided herein comprise at least 2, 3, 4, 5, 6, 7, 8, 9, 10, 11, 12, 13, 14, 15, 16, 17, 18, 19 or 20 T cell epitopes. For example, in some embodiments, the peptides provided herein comprise two or more of the T cell epitopes connected by linkers (e.g., poly peptide linkers).

In some embodiments, the sequence of the peptides comprises a viral protein sequence except for 1 or more (e.g., 1, 2, 3, 4, 5, 6, 7, 8, 9, 10 or more) conservative sequence modifications. As used herein, the term "conservative sequence modifications" is intended to refer to amino acid modifications that do not significantly affect or alter the interaction between a T cell receptor (TCR) and a peptide containing the amino acid sequence presented on an MHC. Such conservative modifications include amino acid substitutions, additions (e.g., additions of amino acids to the N or C terminus of the peptide) and deletions (e.g., deletions of amino acids from the N or C terminus of the peptide). Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues of the peptides described herein can be replaced with other amino acid residues from the same side chain family and the altered peptide can be tested for retention of TCR binding using methods known in the art. Modifications can be introduced into an antibody by standard techniques known in the art, such as site-directed mutagenesis and PCR-mediated mutagenesis.

In some embodiments, the peptides provided herein comprise a sequence that is at least 80%, 85%, 90%, 95% or 100% identical to a protein sequence (e.g., the sequence of a fragment of a viral protein). To determine the percent identity of two amino acid sequences, the sequences are aligned for optimal comparison purposes (e.g., gaps can be introduced in one or both of a first and a second amino acid sequence for optimal alignment and non-identical sequences can be disregarded for comparison purposes). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

In some embodiments, the peptide is chimeric or fusion peptide. As used herein, a "chimeric peptide" or "fusion peptide" comprises a peptide having a sequence provided herein linked to a distinct peptide having sequence to which it is not linked in nature. For example, the distinct peptide can be fused to the N-terminus or C-terminus of the peptide provided herein either directly, through a peptide bond, or indirectly through a chemical linker. In some embodiments, the peptide of the provided herein is linked to another peptide comprising a distinct epitopes. In some embodiments, the peptide provided herein is linked to peptides comprising epitopes from other viral and/or infectious diseases.

A chimeric or fusion peptide provided herein can be produced by standard recombinant DNA techniques. For example, DNA fragments coding for the different peptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, Ausubel et al., eds., John Wiley & Sons; 1992). Moreover, many expression vectors are commercially available that already encode a fusion moiety.

The peptides provided herein can be isolated from cells or tissue sources by an appropriate purification scheme using standard protein purification techniques, and can be produced by recombinant DNA techniques, and/or can be chemically synthesized using standard peptide synthesis techniques. The peptides described herein can be produced in prokaryotic or eukaryotic host cells by expression of nucleotides encoding a peptide(s) of the present invention. Alternatively, such peptides can be synthesized by chemical methods. Methods for expression of heterologous peptides in recombinant hosts, chemical synthesis of peptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987). Academic Press, Inc., San Diego, Calif.; Merrifield. J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu. Rev. Biochem. 57:957; and Offord, R. E. (1980) Semisynthetic Proteins, Wiley Publishing, which are incorporated herein by reference.

In certain aspects, provided herein are nucleic acid molecules encoding the peptides described herein. In some embodiments, the nucleic acid molecule is a vector. In some embodiments, the nucleic acid molecule is a viral vector, such as an adenovirus based expression vector, that comprises the nucleic acid molecules described herein. In some embodiments, the vector provided herein encodes a plurality of epitopes provided herein (e.g., as a polyepitope). In some embodiments, the vector provided herein encodes at least 2, 3, 4, 5, 6, 7, 8, 9, 10, 11, 12, 13, 14, 15, 16, 17, 18, 19 or 20 epitopes provided herein (e.g., epitopes provided in Table 1).

In some embodiments, the vector is AdE1-LMPpoly. The AdE1-LMPpoly vector encodes a polyepitope of defined CTL epitopes from LMP1 and LMP2 fused to a Gly-Ala repeat-depleted EBNA1 sequence. The AdE1-LMPpoly vector is described, for example, in Smith et al., *Cancer Research* 72:1116 (2012); Duraiswamy et al., *Cancer Research* 64:1483-9 (2004); and Smith et al., *J. Immunol* 117:4897-906, each of which is hereby incorporated by reference.

As used herein, the term "vector," refers to a nucleic acid molecule capable of transporting another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication, episomal mammalian vectors). Other vectors (e.g., non-episomal mammalian vectors) can be integrated into the genome of a host cell upon introduction into the host cell, and thereby be replicated along with the host genome. Moreover, certain vectors are capable of directing the expression of genes. Such vectors are referred to herein as "recombinant expression vectors" (or simply, "expression vectors"). In some embodiments, provided herein are nucleic acids operably linked to one or more regulatory sequences (e.g., a promotor) in an expression vector. In some embodiments, the cell transcribes the nucleic acid provided herein and thereby expresses a peptide described herein. The nucleic acid molecule can be integrated into the genome of the cell or it can be extrachromasomal.

In some embodiments, provided herein are cells that contain a nucleic acid described herein (e.g., a nucleic acid encoding a peptide described herein). The cell can be, for example, prokaryotic, eukaryotic, mammalian, avian, murine and/or human. In some embodiments, the cell is a mammalian cell. In some embodiments the cell is an APC (e.g., an antigen-presenting T cell, a dendritic cell, a B cell, or an aK562 cell). In the present methods, a nucleic acid described herein can be administered to the cell, for example, as nucleic acid without delivery vehicle, in combination with a delivery reagent. In some embodiments, any nucleic acid delivery method known in the art can be used in the methods described herein. Suitable delivery reagents include, but are not limited to, e.g., the Mirus Transit TKO lipophilic reagent; lipofectin; lipofectamine; cellfectin; polycations (e.g., polylysine), atelocollagen, nanoplexes and liposomes. In some embodiments of the methods described herein, liposomes are used to deliver a nucleic acid to a cell or subject. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are herein incorporated by reference.

Therapeutic Methods

In some embodiments, the provided herein are methods of treating a cancer, an infection or an autoimmune disorder in a subject by administering to the subject a sample selected according to a method described herein and/or peptide-specific T cells from a sample selected according to a method provided herein.

In some embodiments, the methods provided herein can be used to treat any disease or disorder (e.g., cancer). Examples of cancers include some embodiments, the methods and T cells (e.g., CTLs, CD8 T cells, and/or CD4 T cells) described herein may be used to treat any cancerous or pre-cancerous tumor. In some embodiments, the cancer includes a solid tumor. Cancers that may be treated by methods and compositions provided herein include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma;

adenocarcinoma; gastrinoma, malignant cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometrioid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; mammary paget's disease; acinar cell carcinoma; adenosquamous carcinoma; adenocarcinoma w/squamous metaplasia; malignant thymoma; malignant ovarian stromal tumor; malignant thecoma; malignant granulosa cell tumor; and malignant roblastoma; sertoli cell carcinoma; malignant leydig cell tumor; malignant lipid cell tumor; malignant paraganglioma; malignant extra-mammary paraganglioma; pheochromocytoma; glomangiosarcoma; malignant melanoma; amelanotic melanoma; superficial spreading melanoma; malignant melanoma in giant pigmented nevus; epithelioid cell melanoma; malignant blue nevus; sarcoma; fibrosarcoma; malignant fibrous histiocytoma; myxosarcoma; liposarcoma; leiomyosarcoma; rhabdomyosarcoma; embryonal rhabdomyosarcoma; alveolar rhabdomyosarcoma; stromal sarcoma; malignant mixed tumor; mullerian mixed tumor; nephroblastoma; hepatoblastoma; carcinosarcoma; malignant mesenchymoma; malignant brenner tumor; malignant phyllodes tumor; synovial sarcoma; malignant mesothelioma; dysgerminoma; embryonal carcinoma; malignant teratoma; malignant struma ovarii; choriocarcinoma; malignant mesonephroma; hemangiosarcoma; malignant hemangioendothelioma; kaposi's sarcoma; malignant hemangiopericytoma; lymphangiosarcoma; osteosarcoma; juxtacortical osteosarcoma; chondrosarcoma; malignant chondroblastoma; mesenchymal chondrosarcoma; giant cell tumor of bone; ewing's sarcoma; malignant odontogenic tumor; ameloblastic odontosarcoma; malignant ameloblastoma; ameloblastic fibrosarcoma; malignant pinealoma; chordoma; malignant glioma; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; malignant meningioma; neurofibrosarcoma; malignant neurilemmoma; malignant granular cell tumor; malignant lymphoma; Hodgkin's disease; Hodgkin's lymphoma; paragranuloma; small lymphocytic malignant lymphoma; diffuse large cell malignant lymphoma; follicular malignant lymphoma; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the methods provided herein are used to treat EBV-associated cancer. In some embodiments, the EBV-associated cancer is EBV-associated nasopharyngeal carcinoma, post-transplant lymphoproliferative disorder (PTLD), NK/T cell lymphoma, EBV+ gastric cancer, or EBV+ leiomyosarcoma. In some embodiments, the subject has PTLD and immunodeficiency disorder (e.g., HIV/AIDS or X-linked inhibitor Apoptosis (XIAP)). In some embodiments, the subject is in remission. In some embodiments, the subject has no radiographically or molecularly detectable disease but where the subject remains at high risk of relapse.

In some embodiments, provided herein are methods to treat autoimmune disease using the T cells (e.g., CD4 T cells or CD8 T cells, such as CTLs) disclosed herein. Examples of autoimmune diseases include, for example, glomerular nephritis, arthritis, dilated cardiomyopathy-like disease, ulceous colitis, Sjogren syndrome. Crohn disease, systemic erythematodes, chronic rheumatoid arthritis, multiple sclerosis, psoriasis, allergic contact dermatitis, polymyositis, pachyderma, periarteritis nodosa, rheumatic fever, vitiligo vulgaris, Behcet disease, Hashimoto disease, Addison disease, dermatomyositis, myasthenia gravis, Reiter syndrome, Graves' disease, anaemia perniciosa, sterility disease, pemphigus, autoimmune thrombopenic purpura, autoimmune hemolytic anemia, active chronic hepatitis, Addison's disease, anti-phospholipid syndrome, atopic allergy, autoimmune atrophic gastritis, achlorhydra autoimmune, celiac disease, Cushing's syndrome, dermatomyositis, discoid lupus erythematosus, Goodpasture's syndrome, Hashimoto's thyroiditis, idiopathic adrenal atrophy, idiopathic thrombocytopenia, insulin-dependent diabetes, Lambert-Eaton syndrome, lupoid hepatitis, lymphopenia, mixed connective tissue disease, pemphigoid, pemphigus vulgaris, pernicious anemia, phacogenic uveitis, polyarteritis nodosa, polyglandular autosyndromes, primary biliary cirrhosis, primary sclerosing cholangitis, Raynaud's syndrome, relapsing polychondritis, Schmidt's syndrome, limited sclcroderma (or crest syndrome), sympathetic ophthalmia, systemic lupus ervthematosis, Takayasu's arteritis, temporal arteritis, thyrotoxicosis, type b insulin resistance, ulcerative colitis and Wegener's granulomatosis.

In some embodiments, the methods provided herein are used to treat MS. In some embodiments, the MS is relapsing-remitting MS, secondary progressive MS, primary progressive MS or progressively relapsing MS.

In some embodiments, the methods provided herein are used to treat a SAD. For example, in certain embodiments, the methods provided herein are used to treat rheumatoid arthritis, systemic lupus erythematosus and/or Sjögren's syndrome.

In some embodiments, the methods provided herein are used to treat IBD. For example, in certain embodiments the methods provided herein are used to treat Crohn's disease (regional bowel disease, e.g., inactive and active forms) and/or ulcerative colitis (e.g., inactive and active forms). In some embodiments, the methods provided herein are used to treat irritable bowel syndrome, microscopic colitis, lymphocytic-plasmocytic enteritis, coeliac disease, collagenous colitis, lymphocytic colitis, eosinophilic enterocolitis, indeterminate colitis, infectious colitis (viral, bacterial or protozoan, e.g., amoebic colitis) (e.g., clostridium dificile colitis), pseudomembranous colitis (necrotizing colitis), ischemic inflammatory bowel disease, Behcet's disease, sarcoidosis, scleroderma, IBD-associated dysplasia, dysplasia-associated masses or lesions, and/or primary sclerosing cholangitis.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

In some embodiments, the subject has been exposed to a virus (e.g., EBV or CMV) such that virus particles are detectable in the subject's blood. In some embodiments, the method further comprises measuring viral load in the subject (e.g., before or after administering the peptide-specific T cells (e.g., CD4 T cells or CD8 T cells, such as CTLs) to the subject). Determining viral load in a subject may be a good prognostic marker for immunotherapy effectiveness. In some embodiments, selecting T cells (e.g., CD4 T cells or CD8 T cells, such as CTLs) further comprises determining the number of viral DNA copies in the subject (e.g., in a tissue or blood sample). In some embodiments, viral load is measured two or more times.

In some embodiments, the method includes selecting allogeneic T cells (e.g., CD4 T cells or CD8 T cells, such as CTLs) from a cell bank (e.g., a pre-generated third party donor derived bank of epitope-specific CTLs) for adoptive immunotherapy by determining the level expression of a biomarker with in the CTL population. In some embodiments, the level of expression of two or more biomarkers is determined. In some embodiments, the method further includes selecting allogeneic T cells (e.g., CD4 T cells or CD8 T cells, such as CTLs) because they express a TCR restricted to a class 1 MHC that is encoded by an HLA allele that is present in the subject. In some embodiments, the T cells (e.g., CD4 T cells or CD8 T cells, such as CTLs) are selected if the T cells (e.g., CD4 T cells or CD8 T cells, such as CTLs) and subject share at least 2 (e.g., at least 3, at least 4, at least 5, at least 6) HLA alleles and the CTLs are restricted through a shared HLA allele. In some embodiments, the method comprises testing the TCR repertoire of the pre-generated third-party-donor-derived epitope-specific T cells (i.e., allogeneic T cells) with flow cytometry. In some embodiments epitope-specific T cells are detected using a tetramer assay, an ELISA assay, a western blot assay, a fluorescent microscopy assay, an Edman degradation assay and/or a mass spectrometry assay (e.g., protein sequencing). In some embodiments, the TCR repertoire is analyzed using a nucleic acid probe, a nucleic acid amplification assay and/or a sequencing assay.

EXEMPLIFICATION

Example 1

Fifty-two nasopharyngeal carcinoma (NPC) patients were enrolled in a study applying LMP1&2 and EBNA1-specific CTL immunotherapy for the treatment of EBV-associated NPC, including 41 with active progressive disease following pallatative chemotherapy (active recurrent/metastatic disease, or ARMD) and 11 patients with minimal or no residual disease (N/MRD) following standard radio/chemotherapeutic treatment.

Twenty active disease patients and 9 N/MRD patients received the minimum 2 doses (range 2-8 doses) and a median total of $1.1 \times 10^1$ cells (range: $5.7 \times 10^7$ to $2.4 \times 10^8$). The clinical characteristics of the patients who received adoptive T cell therapy are provided in Table 1 and 2. Of the remaining 23 patients, 1 patient died after the administration of a single dose, T cell therapy was manufactured for 5 patients but not administered due to illness, 12 failed to meet release criteria due to low specificity or cell yield and 5 were withdrawn prior to the commencement of T cell manufacture.

To generate LMP/EBNA1-specific T cells 100-300 mL of peripheral blood was harvested and used to generate peripheral blood mononuclear cells (PBMC). The AdE1-LMPpoly vector was then used to infect 30% of the PBMC (MOI of 10:1) that were then irradiated and co-cultured with the remaining PBMC for two weeks. Cultures were supplemented with fresh growth medium and 120 IU/mL of recombinant IL-2 every 3-4 days (Komtur Pharmaceuticals, Frieburg, Germany). Cultured T cells were tested for antigen specificity using intracellular cytokine analysis and microbial contamination prior to release for infusion.

Polychromatic profiling was performed to characterize the T cells administered to the subjects. MHC tetramers were generated in house. T cells were incubated for 20 minutes at 4° C. with APC-labelled MHC class I tetramers specific for the HLA A11-restricted epitope SSCSSCPLSKI (LMP2A), the HLA A24 restricted epitope TYGPVFMCL (LMP2A) and the HLA Cw03 restricted epitope FVYGGSKTSL (EBNA1). For the assessment of surface phenotype cells were then incubated for a further 30 minutes with the following antibodies: V500-conjugated anti-CD8, PECy7-conjugated anti-CD4 and AF700-conjugated anti-CD3: or with V500-conjugated anti-CD8, AF700-conjugated anti-CD4, PECy7-conjugated anti-CD56, eFluor 450-conjugated anti-CD19 and -conjugated anti-CD14; or with V500-conjugated anti-CD8, PECy7-conjugated anti-CD4, Biotin-conjugated anti-CD57 followed by Steptavidin Cascade Yellow, PE-conjugated anti-CD27, perCPCy5.5-conjugated anti-CD28, FITC-conjugated anti-CD45RA and AF700-conjugated anti-CCR7; or with V500-conjugated anti-CD8, PECy7-conjugated anti-CD4, PE-conjugated anti-TIM3, FITC conjugated anti-LAG3 and BV786-conjugated anti-PD-1. For intracellular analysis, cells were treated with BD TF Fixation/Permeabilisation buffer and then stained in the presence Perm/Wash with the following antibodies: BV421-conjugated anti-Perforin, AF700-conjugated anti-Granzyme B and FITC-conjugated anti-Granzyme K, or BV421-conjugated anti-CTLA-4. Cells were acquired using a BD LSR Fortessa with FACSDiva software (BD Biosciences) and post-acquisition analysis was performed using FlowJo software (TreeStar). As seen in FIG. 1, the E1-LMPpoly expanded T cells were functionally competent.

As seen in FIG. 1, the level of expression of GzmB, GzmK, Prf, PD-1, TIM-3, LAG-3 and/or CTLA4 can be determined in T cells prior to use in adoptive immunotherapy.

Figure 2:
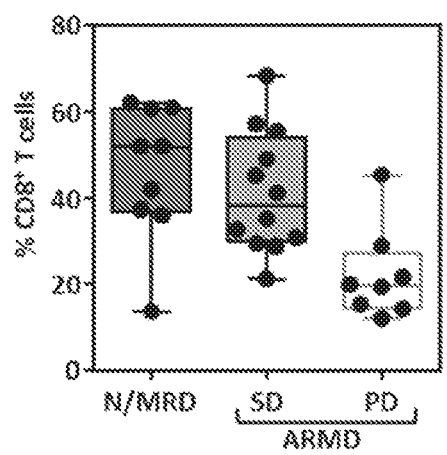
FIG. 2 has two panels and shows the T cell phenotype of CTL compositions administered to patients who had minimal residual disease (N/MRD) and patients who had active-recurrent/metastatic disease (ARMD). ARMD patients either achieved stable disease (SD) or continued to show progressive disease (PD) after CTL immunotherapy. Panel A shows the percentage of CD8-positive T cells in the CTL immunotherapy administered, while panel B shows the total number of LMP/EBNA-1-specific T cells in the CTL immunotherapy administered.
Figure 2:
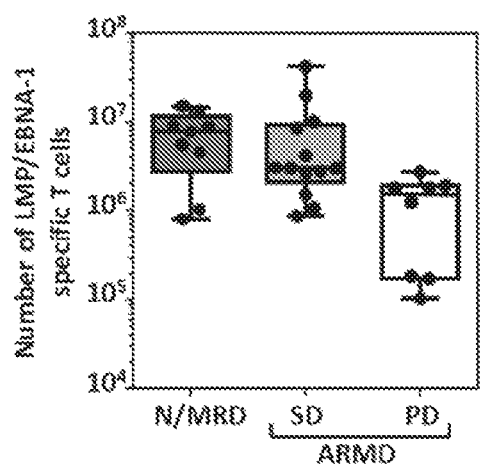
Figure 3:
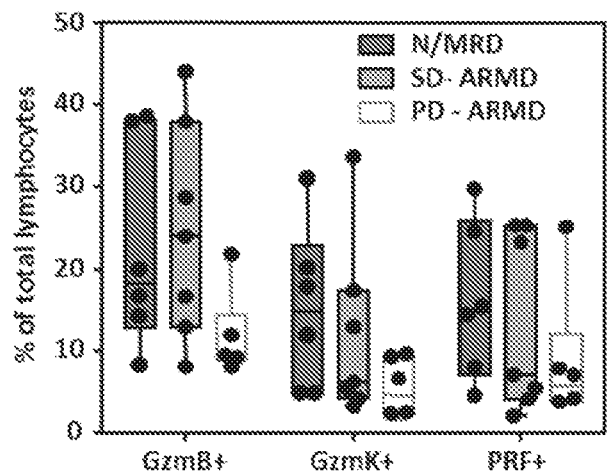
FIG. 3 has two panels and shows the T cell phenotype of CTL compositions administered to patients who had minimal residual disease (N/MRD) and patients who had active-recurrent/metastatic disease (ARMD). ARMD patients either achieved stable disease (SD) or continued to show progressive disease (PD) CTL immunotherapy. Panel A shows the percentage of granzyme B positive (GzmB+) granzyme K positive (GzmK+) and perforin positive (PRF+) lymphocytes in the CTL immunotherapy administered. Panel B shows the percentage of PD-1 positive, TIM-3 positive. LAG-3 positive and CTLA-4 positive lymphocytes in the CTL immunotherapy administered.
Figure 3:
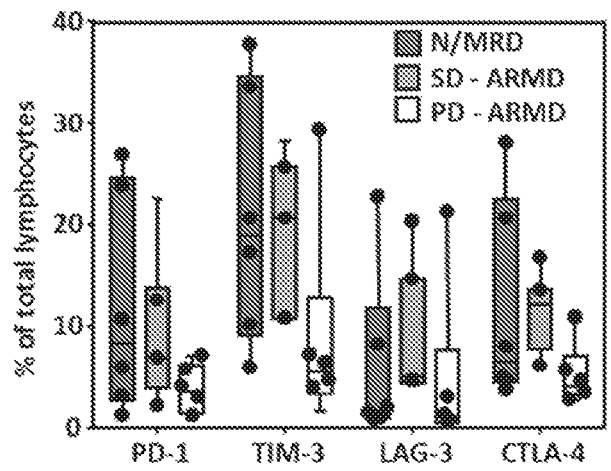

ARMD patients were divided into two groups: patients who achieved stable disease (referred to as SD) and patients who continued to show progressive disease (referred to as PD) after CTL immunotherapy. Circles represent individual patients. As seen in FIG. 2, ARMD patients who received CTL compositions with a greater percentage of CD8$^+$ T cells and/or a greater number of LMP/EBNA-1-specific T cells were more likely to have disease stabilization. Similarly, as seen in FIG. 3, ARMD patients who received CTL compositions with greater GzmB, GzmK, Prf, PD-1, TIM-3, LAG-3 and/or CTLA4 expression were also more likely to have disease stabilization.

Example 2

Autologous EBV-specific T cell therapy was used to treat patients with progressive MS. Each patient received their own T cells stimulated ex vivo to enhance reactivity to EBNA1, LMP1 and LMP2A and their clinical response was monitored. Following ex vivo stimulation, and prior to administration, the T cell samples were assessed for expression of CD107a, interferon gamma (IFNg), interleukin 2 (IL-2), tumor necrosis factor (TNF), granzyme B (GzmB) granzyme K (GzmK) and perforin (Prf) by FACs. Four escalating dose infusions were administered biweekly. Outcome measures were as follows: vital signs; changes in neurological symptoms; neurological examination, including EDSS; cognitive assessment; fatigue assessment; screening for depression; quality of life (QOL) assessment; blood testing; MRI of the brain and spinal cord with gadolinium contrast; and CSF analysis of intrathecal IgG production.

Figure 4:
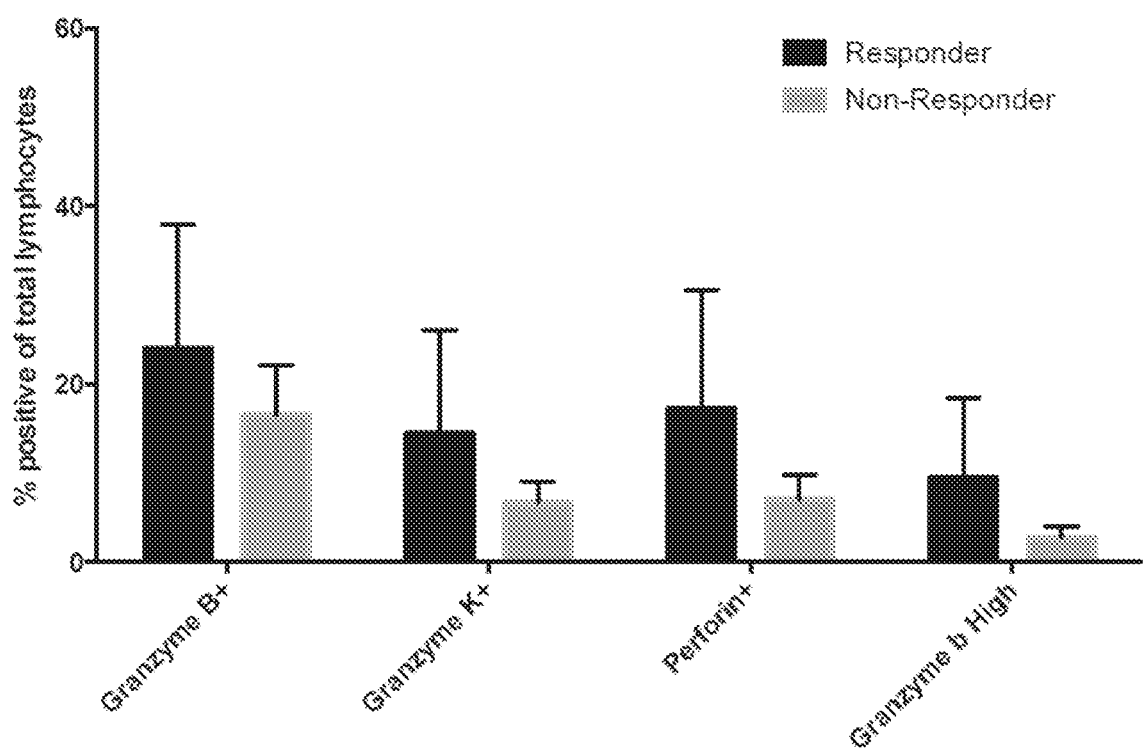
FIG. 4 shows the percentage of CD8 T cells expressing granzyme B (GzmB), granzyme K (GzmK) and/or perforin (Prf).

As seen in FIG. 4, responders tended to have higher percentages of CD8 T cells expressing GzmB, GzmK and Prf compared to non-responders. Additional data reflecting the phenotypic characterization of the adoptively transferred T cells is provided in Table 2.

TABLE 2

Percent of total lymphocytes that express
CD107a, IFNg, IL-2 and TNF (ND = no data)

| Patient | Responder? | CD107a | IFNg | IL-2 | TNF |
|---|---|---|---|---|---|
| 1 | Yes | 0.0% | 0.0% | 0.0% | 0.0% |
| 2 | No | 0.1% | 0.1% | 0.0% | 0.0% |
| 3 | Yes | 8.9% | 8.5% | 5.1% | 9.5% |
| 4 | Yes | 2.5% | 2.3% | 1.4% | 2.4% |
| 5 | Yes | 26.4% | 23.1% | 13.7% | 24.3% |
| 6 | No | 0.1% | 0.1% | 0.0% | 0.1% |
| 7 | ND | 0.0% | 0.0% | ND | 0.0% |
| 8 | ND | 0.0% | 0.0% | ND | 0.0% |
| 9 | ND | 14.3% | 13.2% | ND | 12.7% |

Figure 5:
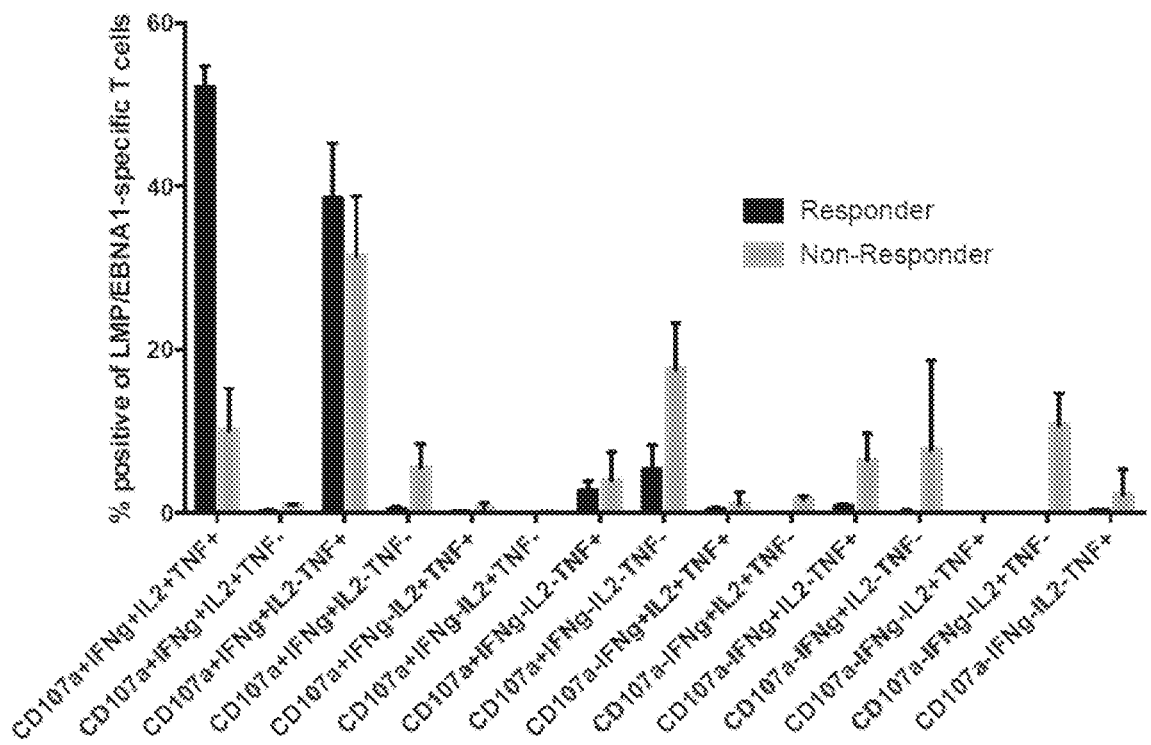
FIG. 5 shows the percentage of LMP/EBNA1-specific T cells in different categories of responders versus non-responders.
Figure 6:
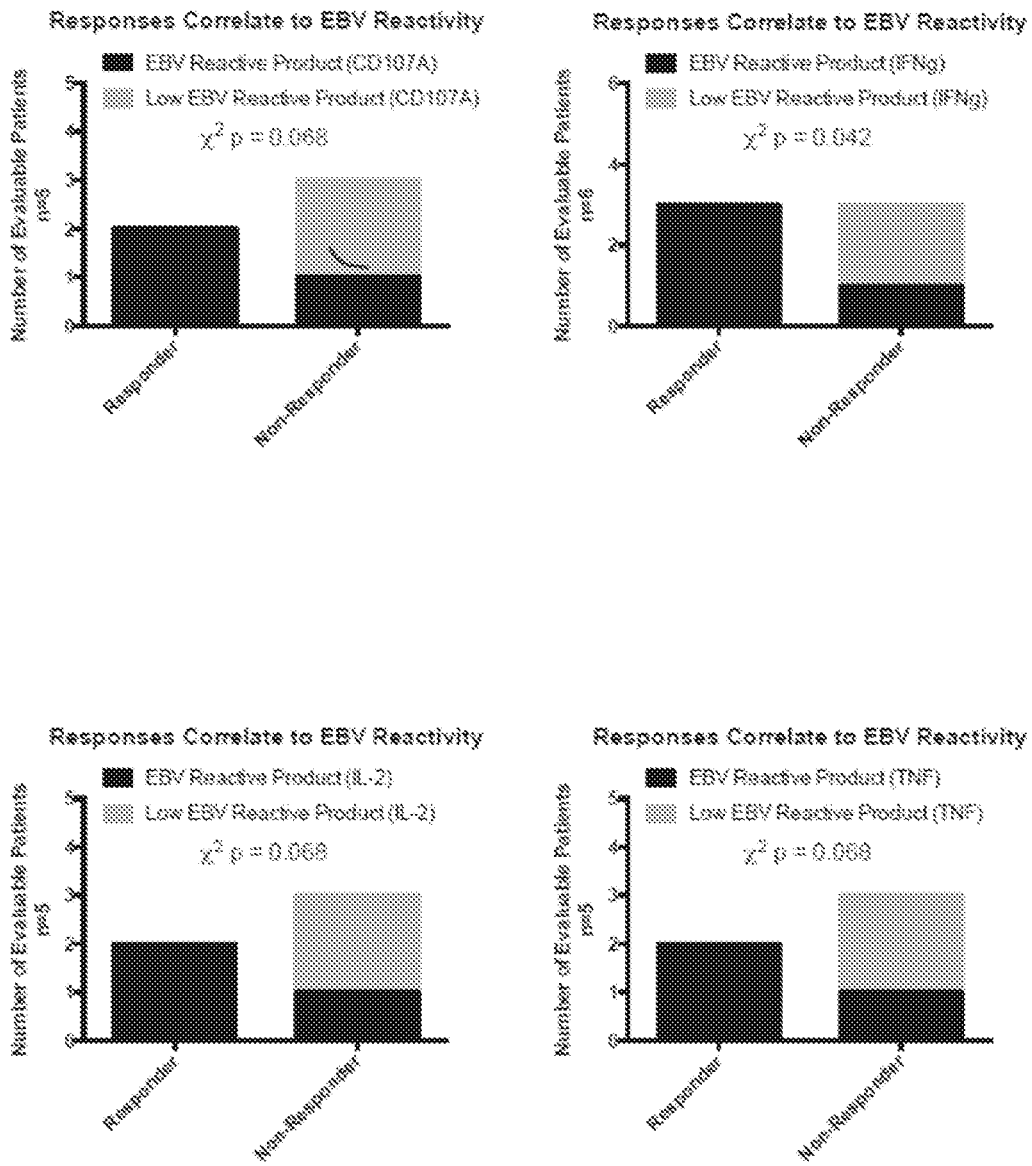
FIG. 6 shows that responses to adoptive immunotherapy correlate to EBV reactivity as measured based on CD107A. IFNg. IL-2 and TNF expression.
Figure 7:
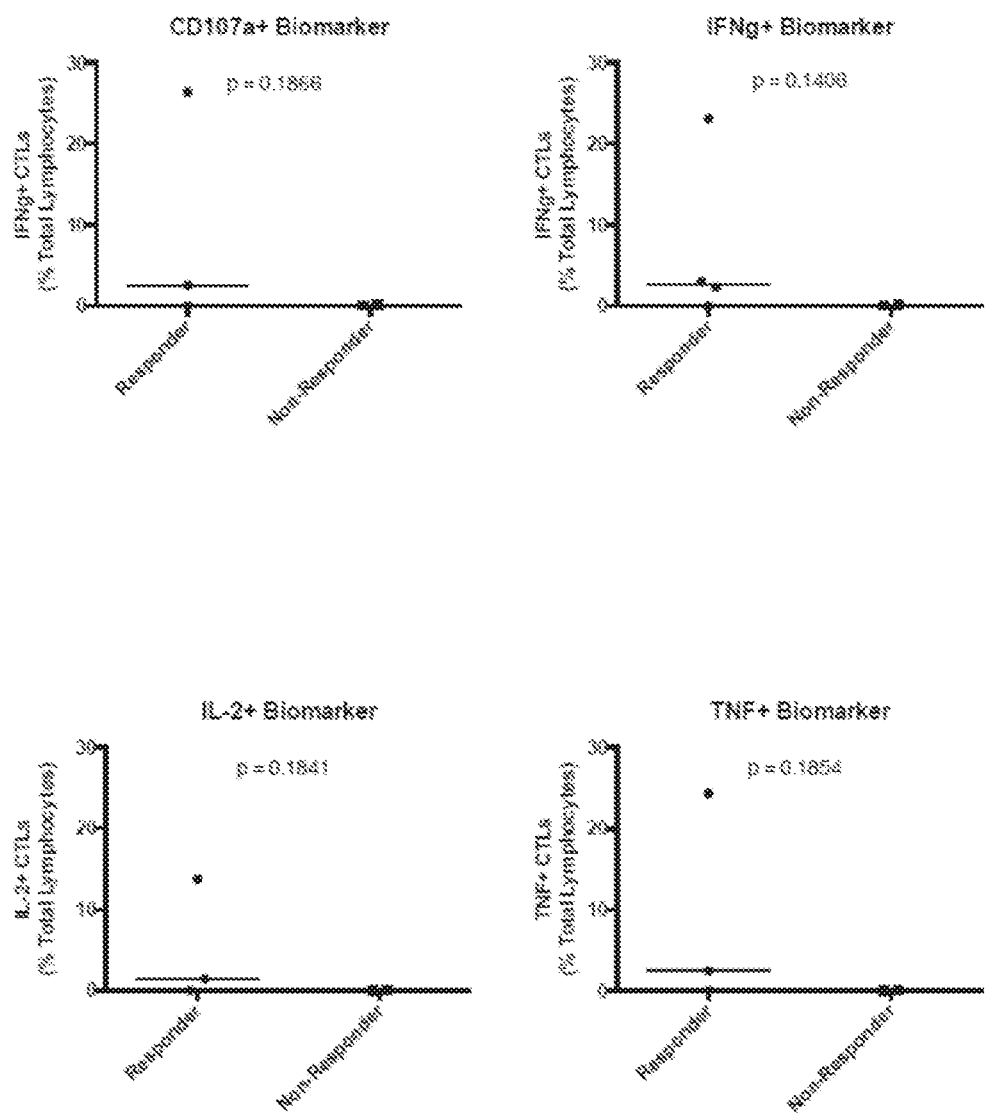
FIG. 7 shows percentage of total lymphocytes expressing CD107a, IFN-γ, IL-2 and/or TNF in responders versus non-responders.
Figure 8:
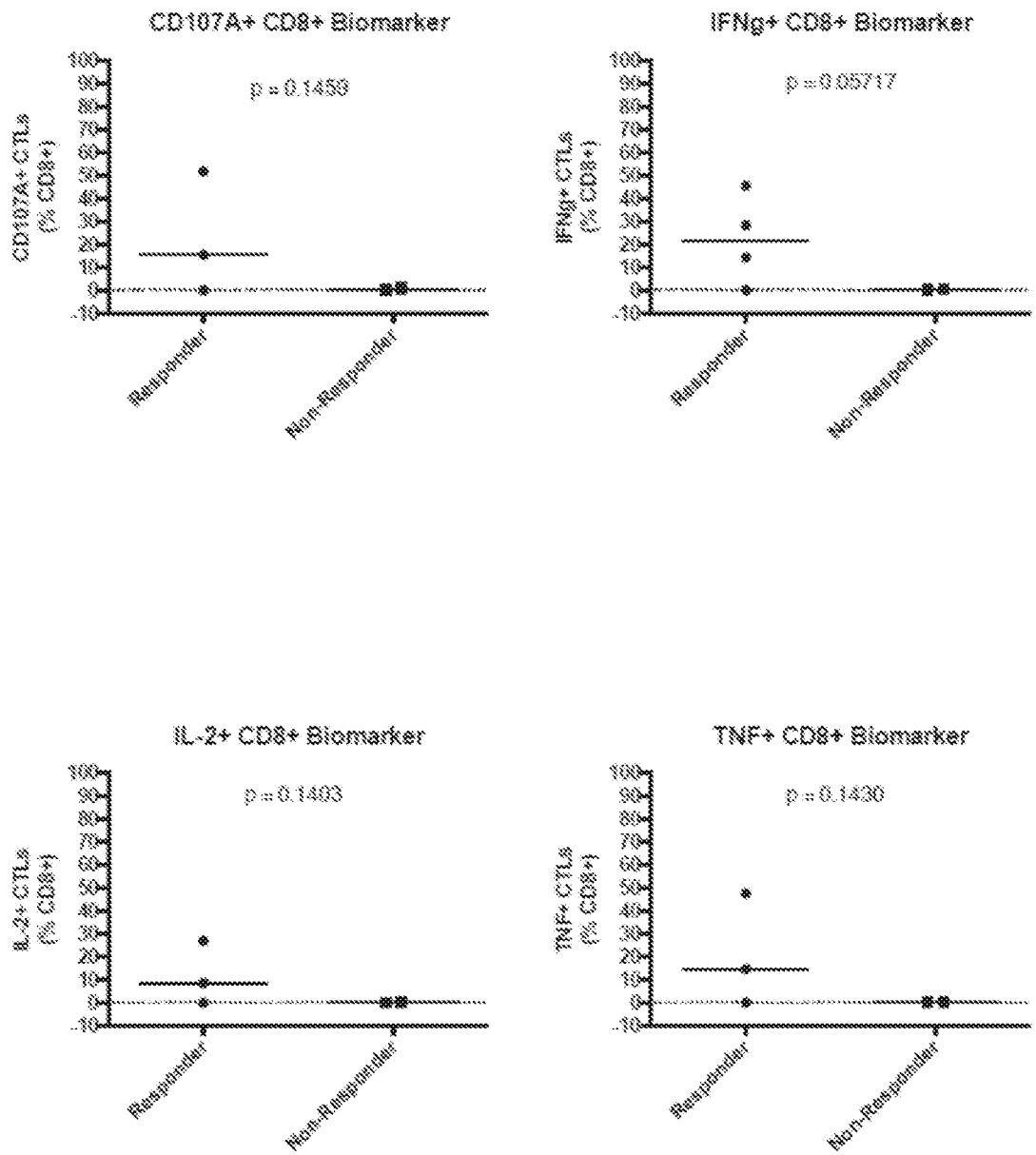
FIG. 8 shows percentage of CD8 T cells expressing CD107a, IFN-γ, IL-2 and/or TNF in responders versus non-responders.
Figure 9:
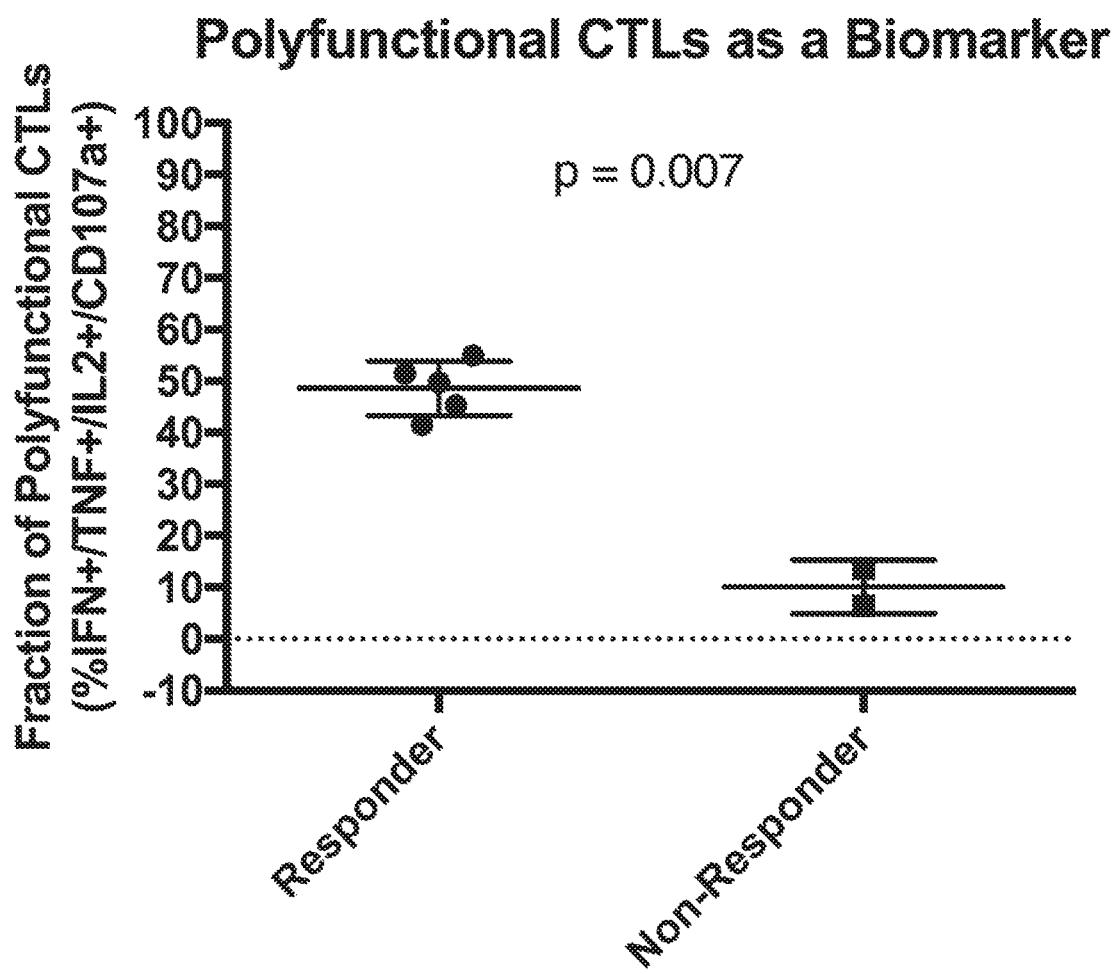
FIG. 9 shows percentage of CD8 T cells expressing CD107a, IFN-γ, IL-2 and TNF in responders versus non-responders.

The percentage of LMP/EBNA1-specific T cells in samples based on patient response and expression of combinations of CD107(a), IFNg, IL-2 and TNF is provided in FIG. 5 and FIG. 9. As can be seen, in these figures, a positive patient response was highly correlated with expression of all four genes by LMP/EBNA1-specific T cells. Notably, patient response correlated with EBV reactivity of the administered T cells, as measured by CD107a, IFNg, IL-2 and TNF expression (FIGS. 6-8). Additional data reflecting the phenotypic characterization of the adoptively transferred T cells is provided in Table 3.

TABLE 3

Percent of CD8 T cells that express CD107a,
IFNg, IL-2 and TNF (ND = no data)

| Patient | Responder? | CD107a | IFNg | IL-2 | TNF |
|---|---|---|---|---|---|
| 1 | Yes | 0.0% | 0.0% | 0.0% | 0.0% |
| 2 | No | 0.8% | 0.7% | 0.2% | 0.4% |
| 3 | Yes | 23.2% | 22.3% | 12.0% | 23.8% |
| 4 | Yes | 13.3% | 14.2% | 8.6% | 14.6% |
| 5 | Yes | 51.7% | 45.5% | 27.0% | 47.8% |
| 6 | No | 0.4% | 0.3% | 0.2% | 0.4% |
| 7 | ND | 0.0% | 0.0% | ND | 0.1% |
| 8 | ND | 0.1% | 0.1% | ND | 0.0% |
| 9 | ND | 32.4% | 29.8% | ND | 28.8% |

All publications, patents, patent applications and sequence accession numbers mentioned herein are hereby incorporated by reference in their entirety as if each individual publication, patent or patent application was specifically and individually indicated to be incorporated by reference. In case of conflict, the present application, including any definitions herein, will control.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of selecting a sample comprising T cells for adoptive immunotherapy or for inclusion in a cell bank, the method comprising determining the expression of IFN-gamma, CD107a, IL-2, TNFalpha, or any combination thereof by total lymphocytes in the sample and selecting the sample for adoptive immunotherapy or for inclusion in a cell bank if at least 0.5% of the total lymphocytes in the sample express any one of IFNgamma, CD107a, IL-2, TNFalpha, or a combination thereof;
wherein the T cells are incubated with antigen-presenting cells to induce proliferation of the T cells before the expression of IFNgamma, CD107a, IL-2, TNFalpha, or any combination thereof by the total lymphocytes is determined, and
wherein the antigen-presenting cells are B cells, antigen-presenting T cells, dendritic cells or aK562 cells.

2. The method of claim 1, wherein the sample comprising T cells is selected from a library of samples, said method comprising screening the library of samples for the expression of IFNgamma, CD107a, IL-2, TNFalpha, or any combination thereof by total lymphocytes in the samples and selecting a sample from the library of samples for adoptive immunotherapy in which at least 0.5% of the total lymphocytes in the sample express IFNgamma, CD107a, IL-2, TNFalpha, or a combination thereof.

3. The method of claim 1, wherein the expression of IFNgamma, CD107a, IL-2, TNFalpha, or any combination thereof is determined by Fluorescence Activated Cell Sorting (FACS) or ELISpot.

4. The method of claim 1, further comprising determining the expression of CD8 by cells in the sample and selecting the sample if at least 20% of the cells express CD8 and/or determining the expression of CD4 by cells in the sample and selecting the sample if at least 10% of the cells express CD4.

5. The method of claim 1, wherein the selected T cells are stored in a cell bank after selection.

6. The method of claim 1, wherein the T cells express a TCR specific for an Epstein-Barr Virus peptide presented on a class I MHC.

7. The method of claim 1, further comprising administration of the selected T cells are administered to a subject in need thereof.

8. The method of claim 7, wherein the subject in need thereof has cancer.

9. The method of claim 8, wherein the cancer is an Epstein-Barr Virus-associated cancer.

10. The method of claim 8, wherein the subject has nasopharyngeal carcinoma, NK/T cell lymphoma, Epstein-Barr Virus-associated gastric carcinoma, or Epstein-Barr Virus-associated leiomyosarcoma.

11. The method of claim 7, wherein the subject in need thereof has post-transplant lymphoproliferative disorder.

12. The method of claim 11, wherein the subject has an autoimmune disorder.

13. The method of claim 12, wherein the autoimmune disorder is multiple sclerosis.

14. The method of claim 7, wherein the T cells are allogeneic to the subject.

15. The method of claim 14, wherein the T cells are obtained from a cell bank.

16. The method of claim 7, wherein the T cells are autologous to the subject.

17. The method of claim 1, wherein the T cells are $CD8^+$ T cells.

18. The method of claim 17, wherein the $CD8^+$ T cells are cytotoxic T cells (CTLs) that express IFNgamma, TNFalpha, IL-2 and CD107a.

19. The method of claim 1, wherein the T cells are $CD4^+$ T cells.

* * * * *